US008932565B2

(12) United States Patent  (10) Patent No.: US 8,932,565 B2
Ilekti et al.  (45) Date of Patent: Jan. 13, 2015

(54) THERMAL COSMETIC TREATMENT PROCESS USING A SEMI-CRYSTALLINE POLYMER

(75) Inventors: Philippe Ilekti, Maison-Alfort (FR); Sylvie Boulogne, L'hay les Roses (FR)

(73) Assignee: L'Oreal, Paris (FR)

( * ) Notice: Subject to any disclaimer, the term of this patent is extended or adjusted under 35 U.S.C. 154(b) by 312 days.

(21) Appl. No.: 12/988,465

(22) PCT Filed: Jul. 22, 2009

(86) PCT No.: PCT/FR2009/051474
§ 371 (c)(1),
(2), (4) Date: Mar. 22, 2011

(87) PCT Pub. No.: WO2010/010301
PCT Pub. Date: Jan. 28, 2010

(65) Prior Publication Data
US 2011/0168199 A1  Jul. 14, 2011

Related U.S. Application Data

(60) Provisional application No. 61/096,393, filed on Sep. 12, 2008.

(30) Foreign Application Priority Data

Jul. 24, 2008 (FR) .................................. 08 55085

(51) Int. Cl.
*A61Q 1/06* (2006.01)
*A61Q 1/04* (2006.01)
*A45D 40/08* (2006.01)
*A61K 8/81* (2006.01)
*A45D 40/18* (2006.01)
*A45D 40/20* (2006.01)

(52) U.S. Cl.
CPC *A61Q 1/06* (2013.01); *A45D 40/08* (2013.01); *A61K 8/8105* (2013.01); *A61K 8/8152* (2013.01); *A45D 40/18* (2013.01); *A45D 40/20* (2013.01); *A45D 2200/155* (2013.01); *A61K 2800/884* (2013.01)
USPC ............................................ 424/64; 424/401

(58) Field of Classification Search
None
See application file for complete search history.

(56) References Cited

U.S. PATENT DOCUMENTS

| | | |
|---|---|---|
| 2,676,182 A | 4/1954 | Daudt et al. |
| 3,148,125 A | 9/1964 | Sabbat |
| 3,627,851 A | 12/1971 | Brady |
| 3,645,705 A | 2/1972 | Miller et al. |
| 3,772,247 A | 11/1973 | Flannigan |
| 4,935,484 A | 6/1990 | Wolfgruber et al. |
| 5,082,706 A | 1/1992 | Tangney |
| 5,110,890 A | 5/1992 | Butler |
| 5,156,911 A | 10/1992 | Stewart |
| 5,171,096 A | 12/1992 | Perrotti |
| 5,221,534 A | 6/1993 | DesLauriers et al. |
| 5,248,739 A | 9/1993 | Schmidt et al. |
| 5,302,685 A | 4/1994 | Tsumura et al. |
| 5,319,040 A | 6/1994 | Wengrovius et al. |
| 5,500,209 A | 3/1996 | Mendolia et al. |
| 5,519,063 A | 5/1996 | Mondet et al. |
| 5,736,125 A | 4/1998 | Morawsky et al. |
| 5,750,723 A | 5/1998 | Eldin et al. |
| 5,783,657 A | 7/1998 | Pavlin et al. |
| 5,817,302 A | 10/1998 | Berthiaume et al. |
| 5,847,156 A | 12/1998 | Eldin et al. |
| 5,874,069 A | 2/1999 | Mendolia et al. |
| 5,919,441 A | 7/1999 | Mendolia et al. |
| 5,981,680 A | 11/1999 | Petroff et al. |
| 5,998,547 A | 12/1999 | Hohner |
| 5,998,570 A | 12/1999 | Pavlin et al. |
| 6,051,216 A | 4/2000 | Barr et al. |
| 6,086,276 A | 7/2000 | Gueret |
| 6,180,123 B1 | 1/2001 | Mondet |
| 6,211,303 B1 | 4/2001 | Hohner |
| 6,340,258 B2 | 1/2002 | Gueret |
| 6,371,673 B1 | 4/2002 | Gueret |
| 6,478,493 B1 | 11/2002 | Cepeda et al. |
| 6,491,927 B1 | 12/2002 | Arnaud et al. |
| 6,949,504 B2 * | 9/2005 | Mondet et al. .................... 514/1 |

(Continued)

FOREIGN PATENT DOCUMENTS

| | | |
|---|---|---|
| DE | 101 50 619 | 4/2003 |
| EP | 542 669 | 5/1993 |

(Continued)

OTHER PUBLICATIONS

International Search Report issued Apr. 8, 2010 in PCT/FR09/051478 filed Jul. 22, 2009.
U.S. Appl. No. 13/003,065, filed Jan. 7, 2011, Ilekti, et al.
U.S. Appl. No. 13/054,681, filed Jan. 18, 2011, Ilekti, et al.
U.S. Appl. No. 13/009,975, filed Jan. 20, 2011, Ilekti, et al.
Anonymous: "Brillants a levres," Research Disclosure Journal, ISSN 0374-4353, vol. 526, No. 20, total 8 pages, (Jan. 25, 2008) XP 007137951.

(Continued)

*Primary Examiner* — Jyothsna Venkat
(74) *Attorney, Agent, or Firm* — Oblon, Spivak, McClelland, Maier & Neustadt, L.L.P.

(57) ABSTRACT

The present invention relates to a non-therapeutic makeup and/or care process for non-fibrous human keratin matter, such as the skin, the lips and the fingernails, comprising the following steps: placing a heating device on or near an outer surface of a lump of a solid cosmetic composition to heat said lump locally in such a way as to soften essentially only said outer surface and lower its coefficient of dynamic friction and then apply the outer surface of the heated composition to the region to be treated, said solid cosmetic composition comprising in a physiologically acceptable medium at least one semi-crystalline polymer.

17 Claims, 3 Drawing Sheets

(56) References Cited

U.S. PATENT DOCUMENTS

Figure 8:
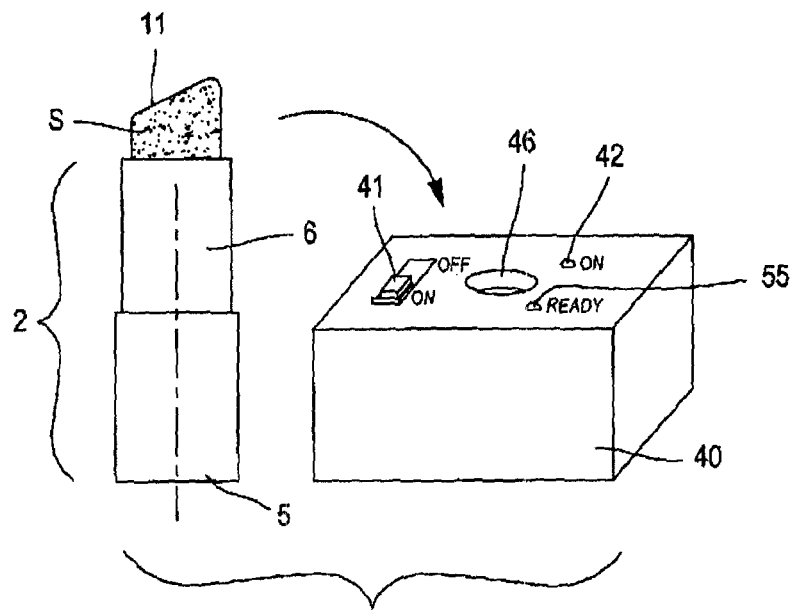

| | | |
|---|---|---|
| 7,293,926 B2 | 11/2007 | Gueret |
| 2002/0005562 A1 | 1/2002 | Kim et al. |
| 2002/0197220 A1 | 12/2002 | Mondet et al. |
| 2003/0072730 A1 | 4/2003 | Tournilhac |
| 2004/0241121 A1* | 12/2004 | Blin et al. ............... 424/70.11 |
| 2005/0031400 A1* | 2/2005 | Marcotte et al. ............. 401/129 |
| 2005/0050328 A1 | 3/2005 | Mizrah |
| 2005/0287105 A1 | 12/2005 | Blin et al. |
| 2006/0008441 A1 | 1/2006 | Kanji et al. |
| 2007/0031361 A1 | 2/2007 | Herrmann et al. |
| 2007/0053859 A1 | 3/2007 | Bui et al. |
| 2007/0286665 A1 | 12/2007 | Bouix et al. |
| 2008/0143214 A1* | 6/2008 | McNamara et al. ........... 310/318 |
| 2008/0152678 A1 | 6/2008 | Shah et al. |
| 2010/0316587 A1 | 12/2010 | Barba et al. |

FOREIGN PATENT DOCUMENTS

| | | |
|---|---|---|
| EP | 0 550 745 | 7/1993 |
| EP | 571 882 | 12/1993 |
| EP | 0 787 730 | 8/1997 |
| EP | 0 951 897 | 10/1999 |
| EP | 1 454 612 | 9/2004 |
| FR | 2 792 190 | 10/2000 |
| FR | 2 824 263 | 11/2002 |
| FR | 2 824 264 | 11/2002 |
| FR | 2 848 422 | 6/2004 |
| FR | 2 888 498 | 1/2007 |
| FR | 2 894 472 | 6/2007 |
| FR | 2 918 272 | 1/2009 |
| FR | 2 926 022 | 7/2009 |
| JP | 2007 269763 | 10/2007 |
| WO | 96 08537 | 3/1996 |
| WO | 01 19333 | 3/2001 |
| WO | 02 47619 | 6/2002 |
| WO | 02 056847 | 7/2002 |
| WO | 2003 106614 | 12/2003 |
| WO | 2005 075542 | 8/2005 |
| WO | 2009 080955 | 7/2009 |
| WO | 2009 104133 | 8/2009 |

OTHER PUBLICATIONS

International Search Report issued Mar. 9, 2010 in PCT/FR09/051474 filed Jul. 22, 2009.

* cited by examiner

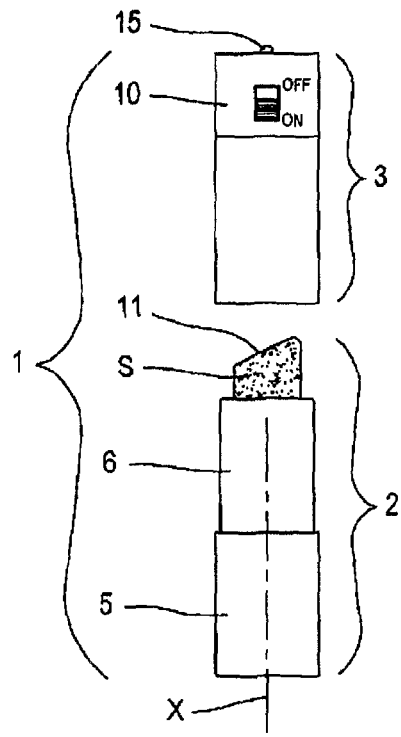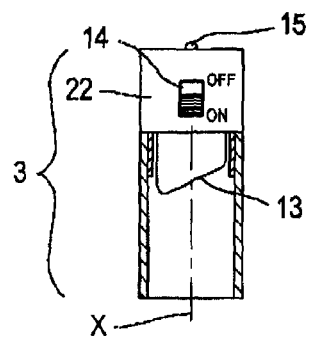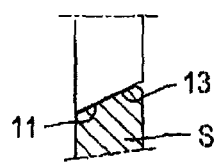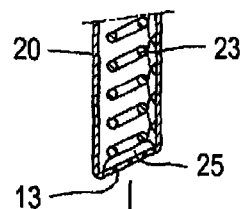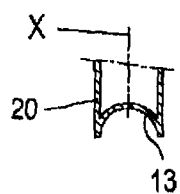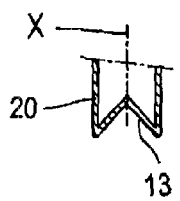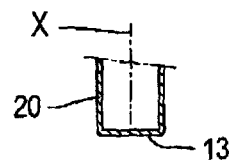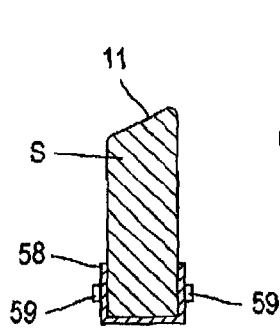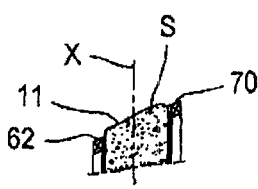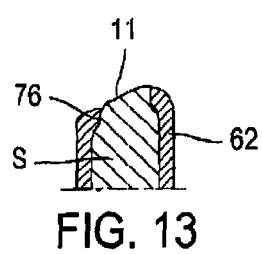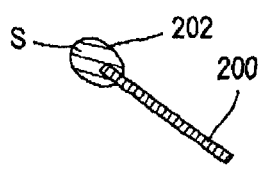

THERMAL COSMETIC TREATMENT PROCESS USING A SEMI-CRYSTALLINE POLYMER

The present invention relates to the field of caring for and/or making up human keratinous substances and more particularly the skin and/or lips.

The development of formulations dedicated to making up and/or caring for the skin and/or lips, having satisfactory properties in terms of application, of comfort, of hold and of coverage and also in terms of makeup effect, such as, for example, gloss, is a permanent objective.

As regards the lips, the lipstick, which appeared at the beginning of the last century, has today established itself and is recognized by users as the predominant application method for making up the lips. This application method offers users a means of choice, in terms of coverage of the lips and of diversity of colors.

Of course, this formulation form must furthermore satisfy requirements, on the one hand, of a mechanical order, in order to ensure the slip and the hold of the stick during application and to prevent it from breaking and, on the other hand, of transfer qualities, in order to guarantee comfortable application and a satisfactory deposited layer of good quality on the lips.

In point of fact, it is known that a number of ingredients capable of contributing advantageous characteristics to the product, in terms of structuring of the composition, for example, may on the other hand be harmful to the makeup effect, in particular gloss.

Thus, it is known that, in order to favor the glossy nature of a composition, it is desirable to reduce the amount of waxes, which, however, detrimentally affects the stability of the stick, which becomes softer and more brittle. Consequently, it is important to find a means for maintaining both the gloss of the deposited layer and the structure of a makeup composition.

In particular, there exists a need to reduce the amount of waxes without furthermore affecting the structuring properties of the composition.

There also exists a need to improve the performance of a cosmetic product in the form of a solid mass, whether on the sensory level and/or with regard to the makeup result, while retaining, in the product, mechanical properties compatible with the packaging as a stick or in another solid form and with application by friction on the surface to be treated.

In particular, there exists a need for a makeup method which, on the one hand, is capable of providing a glossy effect and/or comfort via the use of compositions comprising a small amount of wax and comprising a semi-crystalline polymer and furthermore exhibiting an appropriate stability and/or hardness and which, on the other hand, also proves to have advantageous qualities in terms of slip on a keratinous substance.

It is specifically an object of the invention to provide a novel makeup and/or care method which makes it possible to satisfy all of the abovementioned requirements.

Thus, according to a first of its aspects, a method for making up and/or for the nontherapeutic care of human keratinous substances, in particular the skin, lips or nails, in which an external surface of a piece of solid cosmetic composition is brought into contact with or into the vicinity of a heating device, so as to heat said piece in a localized fashion for the purpose of softening essentially only said external surface and to lower the dynamic friction coefficient thereof, and the external surface of the composition, thus reheated, is subsequently applied to the region to be treated and in particular to be made up, said solid cosmetic composition comprising, in a physiologically acceptable medium, at least one semi-crystalline polymer.

According to a specific embodiment of the invention, the method is a makeup method.

According to a specific embodiment, the softened external surface is brought into direct contact with the region to be treated and in particular with keratinous substances.

In other words, no applicator is employed in depositing the softened composition.

Within the meaning of the present invention, the term "solid" is understood to mean, in particular at ambient temperature (for example at 20° C.), a composition of high consistency which retains its form during storage, in particular which does not flow under its own weight.

When the composition is in the form of a stick, the external surface can be defined as the end of the latter.

According to a specific embodiment, the method according to the present invention is such that the composition is in the form of a stick, in particular with a diameter of greater than or equal to 8 mm.

According to yet another embodiment, the method according to the present invention is such that the composition is a lipstick.

The composition is advantageously characterized by a hardness as defined below.

According to yet another aspect, the invention relates to a kit comprising:
- a composition as defined above, and
- a heating device which makes it possible to locally heat a surface of a piece of said composition.

The piece of composition can be permanently in contact with or close to the heating device and the latter can be activated prior to the application of the composition, in order to raise the temperature of the external surface of the piece of composition. In an alternative form, the piece of composition is brought into contact with or close to the heating device only for use, for the purpose of the application of the composition.

Thus, the invention can make it possible to surface heat, immediately before application, for example the top of the beveled edge of a stick of lipstick produced with a composition according to the invention, in order to make possible the deposition, this being the case even if the stick comprises compounds relatively unfavorable to satisfactory application under cold conditions, these compounds contributing enhanced performances in terms of hold and/or gloss.

In implementational examples of the invention, it is possible, by reheating the surface of the stick, to improve its slip and thus its application on the lips or skin.

According to a specific embodiment, the composition employed according to the invention exhibits a temperature-sensitive dynamic friction coefficient of greater than or equal to 0.5 to 25° C., better still of greater than or equal to 0.6 to 25° C.

The solid composition advantageously exhibits a hardness of greater than or equal to 80 N·m$^{-1}$ at 20° C., better still of greater than or equal to 100 N·m$^{-1}$, indeed even 120 N·m$^{-1}$, at 20° C., which renders the stick mechanically strong and allows it to be packaged, for example, in a conventional tube comprising two parts which can rotate with respect to one another in order to move the stick.

The dynamic friction coefficient can be, at the temperature to which the composition is heated, less than or equal to 0.45, better still 0.4.

The dynamic friction coefficient, which is greater than or equal to 0.5 at 25° C., can thus become, for example, less than or equal to 0.45 at 45° C., that is to say can reach a value comparable to some known lipsticks designed for an application at 25° C.

The invention can be applied to a stick of product comprising an amount of semi-crystalline polymer such that the application thereof under cold conditions and/or without heating is difficult, virtually impossible or unpleasant. For such a stick of product, application after heating becomes possible, with particularly advantageous performances of comfort, indeed even of gloss, from the viewpoint of the presence of the oils which it comprises.

The product can be heated in various ways, for example by being exposed to infrared radiation or to radio frequency radiation.

The product can also be heated by blowing hot air, by being exposed to ultrasonic vibrations or by heat transfer on contact with or close to a hot surface, which will, for example, rest radially against the external surface, in particular the end of the stick. The hot surface can also rest axially against the external surface, in particular the end of the stick. The hot surface can have a beveled, inverted cone or concave hollow, in particular spherical, shape.

The external surface of the product can be heated to a temperature $T_m$ greater than or equal to 40° C., indeed even greater than 45° C. or else greater than 50° C. The external surface can be heated to a temperature $T_m$ of between 40° C. and 95° C., better still from 45° C. to 85° C., even better still from 45° C. to 75° C.

The temperature of the application surface, in particular of the end of the stick, must not cause a risk of burning during application. This is why a waiting time between the moment when the end is heated and the application to the keratinous substances may possibly be necessary.

The difference in temperature between the heated external surface and the portion of the product which remains solid can be greater than or equal to 5° C., better still greater than or equal to 15° C. or 20° C., at least at the beginning of the application, indeed even greater than 30° C.

Only the product can come into contact with the region treated during the application.

The heating device can be housed in a closure cap for the support, so as to make it possible to heat the external surface with the cap in place on the support. The heating device can also be housed elsewhere than in a closure cap for the support.

The heating device can be housed in a case into which the support can be inserted so that the heating can take place when the support is inserted into the case, in particular a case comprising an opening into which the piece of solid product can be inserted, preferably without the whole of the support being positioned inside the case.

The heating device can be integral with the packaging and application device.

The heating device can be arranged in order to come into contact with the external surface.

The heating device can be arranged in order to be traversed by the piece of product, in particular in order to comprise a hot surface of annular shape.

The heating device can comprise a control means allowing the user to control the operation thereof. This control means can comprise a switch present on the support or on a closure cap for the support.

The heating device can comprise an electric resistance in order to heat a surface which can come into contact with the application surface or close to the latter.

The heating device can comprise an infrared emitter arranged so as to subject the application surface to infrared light in order to overheat the surface, and a means for emitting radio frequency radiation which makes it possible to raise the temperature of the external surface, a fan for blowing hot air over the external surface or a source of ultrasound for reheating the external surface.

The heating device can also comprise at least two components capable of producing, when mixed, an exothermic reaction.

The piece of product can be in the stick form and the external surface can be defined by the end of the stick.

The heating device can comprise a source of electrical energy comprising one or more batteries, including storage batteries.

The heating device can comprise an electric generator actuated by the user.

The heating device can comprise means which make it possible to ensure heating of the piece of composition at a predefined temperature, despite the wear of said piece. This means can comprise an elastically deformable member which ensures the contact or a constant distance between the external surface to be heated and the heating device, compensating for the wear of the piece of composition.

These means can also comprise, if appropriate, a temperature sensor which makes it possible to adjust the heating power, for example to increase it if the external surface is further from the heat source.

Dynamic Friction Coefficient

Use may be made, in characterizing the dynamic friction coefficient of a product, of a device comprising a sled which moves over a length of 100 mm on ball bearings.

The satisfactory movement of the sled is provided by virtue of a rigid connection to the movable beam of a tension and compression device (TA-XT2 from Rheo) placed in the horizontal position, via a magnet attached to the rear of the sled.

The product S for which it is desired to evaluate the dynamic friction coefficient is cut at one end with a tungsten wire with a diameter of 250 µm while moving the wire relative to the stick at a rate of 100 mm/min perpendicular to its longitudinal axis, so as to have a contact surface which is flat and parallel to the slip surface W.

A normal force Fn is applied to it at the slip surface W using a weight. This weight is such that the pressure exerted on the surface of the product S in contact with W is $7.9 \times 10^{-3}$ MPa.

The product can be provided in the form of a stick cylindrical in revolution.

In the case where the transverse cross section of the stick is not circular, the stick is made to slip in the direction of the small axis of its cross section, the large axis being moved parallel to itself.

Figure 15:
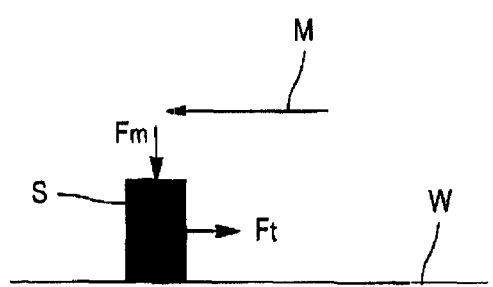

The friction coefficient is defined as the ratio of the tangential force Ft applied to the body set in motion in the direction M to the normal force Fn experienced by the same body, as illustrated in FIG. 15.

In a friction test, it is possible to distinguish a first transitory phase of setting the system in motion and a second steady-state phase.

In the first phase, the tangential force increases to reach a maximum which corresponds to the setting in motion of the system. This maximum corresponds to the static friction force, known as static Ft, and makes it possible to define a static friction coefficient (µs)

$$\mu s = static\ Ft/Fn$$

where Fn is the normal force applied.

The tangential force Ft subsequently decreases to generally reach a more stable state. The dynamic friction coefficient is defined in this phase of the movement as the ratio of the dynamic friction force (tangential force) to the normal force applied (Fn):

$$\mu d = \text{dynamic } Ft/Fn$$

The friction coefficient is a dimensionless quantity which is a function of the two surfaces in contact and of the contact conditions.

The slip surface is defined by artificial skin, with the reference "Bio Skin Plate Black K275" from Macrepos, with a width equal to or greater than that of the cross section of the stick.

For a measurement at 25° C., all the equipment and the composition are at 25° C.

The artificial skin is placed on a support which can be heated to the temperature at which it is desired to measure the dynamic friction coefficient. The stick, initially at the temperature of 25° C., is applied, for example, to the artificial skin thus heated, for example to 45° C., if the measurement has to be carried out at 45° C. The surface temperature of the artificial skin can be monitored with an optical thermometer.

In some embodiments, the dynamic friction coefficient of a composition according to the invention is greater than or equal to 0.6, indeed even 0.7 or 0.8, at 25° C. The dynamic friction coefficient at 25° C. of the compositions according to the invention can be less than or equal to 5.

The stick can have a diameter of 12.7 mm in its region of contact with the slip surface but other values are possible, for example ranging from 7 mm to 50 mm.

Hardness Parameter

The compositions under consideration according to the invention are relatively hard at ambient temperature and, under the action of heat, become soft enough to be applied.

The hardness can be measured at 20° C. by the "cheese wire" method, which consists in transversely cutting a stick of product, preferably cylindrical in revolution, using a stiff tungsten wire with a diameter of 250 µm, the wire being moved relative to the stick at a rate of 100 mm/min. The hardness corresponds to the maximum shear force exerted by the wire on the stick at 20° C., this force being measured using a DFGHS 2 dynamometer from Indelco-Chatillon. The measurement is repeated three times and then averaged.

The mean of the three values measured using the above-mentioned dynamometer, denoted Y, is given in grams. This mean is converted to newtons and then divided by L, which represents the greatest dimension traversed by the wire. In the case of a cylindrical stick, L is equal to the diameter in meters.

The hardness is converted by the following equation:

$$(Y \times 10^{-3} \times 9.8)/L$$

For a measurement at a different temperature, the entire stick is heated to the temperature where the hardness has to be measured.

According to this method, the hardness at 20° C. of examples of composition according to one aspect of the invention is greater than 80 N·m$^{-1}$, in particular greater than 100 N·m$^{-1}$, preferably greater than 120 N·m$^{-1}$.

A composition of the invention is cosmetically or dermatologically acceptable, namely comprises a nontoxic physiologically acceptable medium capable of being applied to the lips of human beings. The term "cosmetically acceptable" is understood to mean, within the meaning of the invention, a composition with a pleasant appearance, a pleasant smell and a pleasant feel, suitable for use in cosmetics.

Semi-Crystalline Polymer

The composition according to the invention can also advantageously comprise at least one semi-crystalline polymer with an organic structure, the melting point of which is greater than or equal to 30° C.

Preferably, the total amount of semi-crystalline polymer(s) represents from 2 to 20% by weight of the total weight of the composition, for example from 3 to 15% by weight and better still from 4 to 10% by weight.

The term "polymers" is understood to mean, within the meaning of the invention, compounds comprising at least 2 repeat units, preferably at least 3 repeat units and more especially at least 10 repeat units.

The term "semi-crystalline polymer" is understood to mean, within the meaning of the invention, polymers comprising a crystallizable part and an amorphous part and exhibiting a first-order reversible phase change temperature, in particular a melting point (solid-liquid transition). The crystallizable part is either a side chain (or a pendent chain) or a block in the backbone.

When the crystallizable part of the semi-crystalline polymer is a block of the polymer backbone, this crystallizable block is different in chemical nature from the amorphous blocks; in this case, the semi-crystalline polymer is a block copolymer, for example of the diblock, triblock or multiblock type. When the crystallizable part is a chain pendent to the backbone, the semi-crystalline polymer can be a homopolymer or a copolymer.

The term "organic compound" or "with an organic structure" is understood to mean compounds comprising carbon atoms and hydrogen atoms and optionally heteroatoms, such as S, O, N or P, alone or in combination.

The melting point of the semi-crystalline polymer is preferably less than 150° C.

The melting point of the semi-crystalline polymer is preferably greater than or equal to 30° C. and less than 100° C. More preferably, the melting point of the semi-crystalline polymer is preferably greater than or equal to 30° C. and less than 70° C.

The semi-crystalline polymer or polymers according to the invention which are used are solids at ambient temperature (25° C.) and atmospheric pressure (760 mmHg), the melting points of which are greater than or equal to 30° C. The melting point values correspond to the melting point measured using a differential scanning calorimeter (DSC), such as the calorimeter sold under the name DSC30 by Mettler, with a rise in temperature of 5 or 10° C. per minute (the melting point considered is the point corresponding to the temperature of the most endothermic peak of the thermogram).

The semi-crystalline polymer or polymers according to the invention preferably have a melting point which is greater than the temperature of the keratinous substrate intended to receive said composition, in particular the skin or lips.

According to the invention, the semi-crystalline polymers are advantageously soluble in the fatty phase, in particular to at least to by weight, at a temperature greater than their melting point. Apart from the crystallizable chains or blocks, the blocks of the polymers are amorphous.

The term "crystallizable chain or block" is understood to mean, within the meaning of the invention, a chain or block which, if it were alone, would change reversibly from the amorphous state to the crystalline state, according to whether the temperature is above or below the melting point. A chain within the meaning of the invention is a group of atoms which is in the pendent or side position with respect to the backbone of the polymer. A block is a group of atoms belonging to the backbone, a group constituting one of the repeat units of the polymer.

The polymer backbone of the semi-crystalline polymers is preferably soluble in the fatty phase at a temperature greater than their melting point.

Preferably, the crystallizable blocks or chains of the semi-crystalline polymers represent at least 30% of the total weight of each polymer and better still at least 40%. The semi-crystalline polymers with crystallizable side chains are homo- or copolymers. The semi-crystalline polymers of the invention with crystallizable blocks are block or multiblock copolymers. They can be obtained by polymerization of monomers with reactive (or ethylenic) double bonds or by polycondensation. When the polymers of the invention are polymers with crystallizable side chains, the latter are advantageously in the statistical or random form.

Preferably, the semi-crystalline polymers of the invention are synthetic in origin.

According to a preferred embodiment, the semi-crystalline polymer is chosen from:
  homopolymers and copolymers comprising units resulting from the polymerization of one or more monomers carrying crystallizable hydrophobic side chain(s),
  polymers carrying, in the backbone, at least one crystallizable block,
  polycondensates of aliphatic or aromatic or aliphatic/aromatic polyester type,
  copolymers of ethylene and of propylene prepared by metallocene catalysis.

The semi-crystalline polymers which can be used in the invention can be chosen in particular from:
  block copolymers of polyolefins with controlled crystallization, the monomers of which are described in EP-A-0 951 897,
  polycondensates and in particular of aliphatic or aromatic or aliphatic/aromatic polyester type,
  copolymers of ethylene and of propylene prepared by metallocene catalysis,
  homo- or copolymers carrying at least one crystallizable side chain and homo- or copolymers carrying, in the backbone, at least one crystallizable block, such as those described in the document U.S. Pat. No. 5,156,911,
  homo- or copolymers carrying at least one crystallizable side chain with in particular fluorinated group(s), such as described in the document WO-A-01/19333,
  and their blends.

In the last two cases, the crystallizable side chain or block or side chains or blocks are hydrophobic.

A) Semi-Crystalline Polymers with Crystallizable Side Chains

Mention may in particular be made of those defined in the documents U.S. Pat. No. 5,156,911 and WO-A-01/19333.

These are homopolymers or copolymers comprising from 50 to 100% by weight of units resulting from the polymerization of one or more monomers carrying a crystallizable hydrophobic side chain.

These homo- or copolymers have any nature provided that they exhibit the conditions indicated below, with in particular the characteristic of being soluble or dispersible in the fatty phase by heating above their melting point M.p. They can result:
  from the polymerization, in particular radical polymerization, of one or more monomers with reactive double bond(s) or ethylenic monomers with respect to polymerization, namely with a vinyl, (meth)acrylic or allyl group,
  from the polycondensation of one or more monomers carrying coreactive groups (carboxylic or sulfonic acid, alcohol, amine or isocyanate groups), such as, for example, polyesters, polyurethanes, polyethers or polyureas.

a) Generally, the crystallizable units (chains or blocks) of the semi-crystalline polymers according to the invention originate from monomer(s) with crystallizable block(s) or chain(s) used for the manufacture of semi-crystalline polymers. These polymers are chosen in particular from the homopolymers and copolymers resulting from the polymerization of at least one monomer with crystallizable chain(s) which can be represented by the formula X:

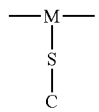

with M representing an atom of the polymer backbone,
C representing a crystallizable group, and
S representing a spacer.

The crystallizable chains "—S—C" can be aliphatic or aromatic and optionally fluorinated or perfluorinated. "C" represents in particular a linear or branched or cyclic $(CH_2)_n$ group with n an integer ranging from 12 to 40. Preferably, "C" is a linear group. Preferably, "S" and "C" are different.

When the crystallizable chains are hydrocarbon aliphatic chains, they comprise hydrocarbon alkyl chains with at least 12 carbon atoms and at most 40 carbon atoms and better still at most 24 carbon atoms. They are in particular aliphatic chains or alkyl chains having at least 12 carbon atoms and preferably they are $C_{14}$-$C_{24}$, preferably $C_{16}$-$C_{22}$, alkyl chains. When they are fluorinated or perfluorinated alkyl chains, they comprise at least 11 carbon atoms, at least 6 carbon atoms of which are fluorinated.

Mention may be made, as example of semi-crystalline homopolymers or copolymers with crystallizable chain(s), of those resulting from the polymerization of one or more following monomers: saturated alkyl (meth)acrylates with the $C_{14}$-$C_{24}$ alkyl group, perfluoroalkyl (meth)acrylates with a $C_{11}$-$C_{15}$ perfluoroalkyl group, N-alkyl(meth)acrylamides with the $C_{14}$ to $C_{24}$ alkyl group, with or without a fluorine atom, vinyl esters with alkyl or perfluoro(alkyl) chains with the $C_{14}$ to $C_{24}$ alkyl group (with at least 6 fluorine atoms per one perfluoroalkyl chain), vinyl ethers with alkyl or perfluoro (alkyl) chains with the $C_{14}$ to $C_{24}$ alkyl group and at least 6 fluorine atoms per one perfluoroalkyl chain, $C_{14}$ to $C_{24}$ α-olefins, such as, for example, octadecene, para-alkylstyrenes with an alkyl group comprising from 12 to 24 carbon atoms, and their mixtures.

When the polymers result from a polycondensation, the crystallizable hydrocarbon and/or fluorinated chains as defined above are carried by a monomer which can be a diacid, a diol, a diamine or a diisocyanate.

When the polymers which are subject matters of the invention are copolymers, they additionally comprise from 0 to 50% of groups Y, which is a polar or nonpolar monomer or a mixture of the two:

When Y is a polar monomer, it is a monomer carrying polyoxyalkylenated groups (in particular oxyethylenated and/or oxypropylenated groups), a hydroxyalkyl (meth)acrylate, such as hydroxyethyl acrylate, (meth)acrylamide, an N-alkyl(meth)acrylamide, an N,N-dialkyl(meth)acrylamide, such as, for example, N,N-diisopropylacrylamide, N-vinylpyrrolidone (NVP), N-vinylcaprolactam, a monomer carrying at least one carboxylic acid group, such as (meth)acrylic acid, crotonic acid, itaconic acid, maleic acid or fumaric acid, or carrying a carboxylic acid anhydride group, such as maleic anhydride, and their mixtures.

When Y is a nonpolar monomer, it can be an ester of the linear, branched or cyclic alkyl (meth)acrylate type, a vinyl ester, an alkyl vinyl ether, an α-olefin, styrene or styrene substituted by a $C_1$-$C_{10}$ alkyl group, such as α-methylstyrene, or a macromonomer of the polyorganosiloxane with vinyl unsaturation type.

The term "alkyl" is understood to mean, within the meaning of the invention, a saturated group, in particular a $C_8$-$C_{24}$ group, unless specifically mentioned.

Preferably, the semi-crystalline polymers with a crystallizable side chain are alkyl (meth)acrylate or alkyl(meth)acrylamide homopolymers with an alkyl group as defined above and in particular a $C_{14}$-$C_{24}$ alkyl group, copolymers of these monomers with a hydrophilic monomer preferably different in nature from (meth)acrylic acid, such as N-vinylpyrrolidone or hydroxyethyl (meth)acrylate, and their blends.

Advantageously, the semi-crystalline polymer or polymers with a crystallizable side chain have a weight-average molecular weight $M_w$ ranging from 5000 to 1 000 000, preferably from 10 000 to 800 000, preferentially from 15 000 to 500 000, more preferably from 100 000 to 200 000.

Mention may be made, as specific example of semi-crystalline polymer which can be used in the composition according to the invention, of the Intelimer® products from Landec described in the brochure "Intelimer® polymers", Landec IP22 (Rev. 4-97). These polymers are in the solid form at ambient temperature (25° C.). They carry crystallizable side chains and exhibit the above formula X. They are poly(($C_{10}$-$C_{30}$)alkyl acrylate)s, which are particularly suitable as semi-crystalline polymers which can be included in a composition in accordance with the present invention. These polymers can in particular exhibit a molecular weight varying from 15 000 to 500 000, preferably from 100 000 to 200 000.

For example, the choice is made of the Intelimer® product IPA 13-1 from Landec, which is a poly(stearyl acrylate) with a molecular weight of approximately 145 000 and a melting point of 49° C.

The semi-crystalline polymers can be in particular those described in examples 3, 4, 5, 7 and 9 of U.S. Pat. No. 5,156,911 and more particularly from the copolymerization:
of acrylic acid, of hexadecyl acrylate and of isodecyl acrylate in a 1/16/3 ratio,
of acrylic acid and of pentadecyl acrylate in a 1/19 ratio,
of acrylic acid, of hexadecyl acrylate and of ethyl acrylate in a 2.5/76.5/20 ratio,
of acrylic acid, of hexadecyl acrylate and of methyl acrylate in a 5/85/10 ratio,
of acrylic acid and of octadecyl methacrylate in a 2.5/97.5 ratio.

Use may also be made of the polymer Structure "O" from National Starch, such as that described in the document U.S. Pat. No. 5,736,125 with a melting point of 44° C.

The semi-crystalline polymers can be in particular semi-crystalline polymers with crystallizable pendent chains comprising fluorinated groups, such as described in examples 1, 4, 6, 7 and 8 of the document WO-A-01/19333.

Use may also be made of the semi-crystalline polymers obtained by copolymerization of stearyl acrylate and of acrylic acid or of NVP as are described in the document U.S. Pat. No. 5,519,063 or EP-A-0 550 745.

Use may also be made of the semi-crystalline polymers obtained by copolymerization of behenyl acrylate and of acrylic acid or of NVP as are described in the documents U.S. Pat. No. 5,519,063 and EP-A-0 550 745 and more especially those described in the polymer preparation examples 3 and 4 below.

B) Polymers Carrying, in the Backbone, at Least One Crystallizable Block

These are again polymers which are soluble or dispersible in the fatty phase by heating above their melting point M.p. These polymers are in particular block copolymers composed of at least two blocks of different chemical natures, one of which is crystallizable.

The polymer carrying, in the backbone, at least one crystallizable block can be chosen from block copolymers of olefin or of cycloolefin with a crystallizable chain, such as those resulting from the block polymerization of:
cyclobutene, cyclohexene, cyclooctene, norbornene (that is to say, bicyclo[2.2.1]hept-2-ene), 5-methylnorbornene, 5-ethylnorbornene, 5,6-dimethylnorbornene, 5,5,6-trimethylnorbornene, 5-ethylidenenorbornene, 5-phenylnorbornene, 5-benzylnorbornene, 5-vinylnorbornene, 1,4,5,8-dimethano-1,2,3,4,4a,5,8a-octahydronaphthalene, dicyclopentadiene or their mixtures, with
ethylene, propylene, 1-butene, 3-methyl-1-butene, 1-hexene, 4-methyl-1-pentene, 1-octene, 1-decene, 1-eicosene or their mixtures,
and in particular copoly(ethylene/norbornene) blocks and (ethylene/propylene/ethylidenenorbornene) terpolymer blocks. Use may also be made of those resulting from the block copolymerization of at least two $C_2$-$C_{16}$ α-olefins and better still $C_2$-$C_{12}$ α-olefins, such as those mentioned above, and in particular the block bipolymers of ethylene and of 1-octene.

The polymer carrying, in the backbone, at least one crystallizable block can be chosen from copolymers exhibiting at least one crystallizable block, the remainder of the copolymer being amorphous (at ambient temperature). These copolymers can, in addition, exhibit two crystallizable blocks of different chemical natures.

The preferred copolymers are those which have, at ambient temperature, both a crystallizable block and a lipophilic amorphous block which are sequentially distributed. Mention may be made, for example, of the polymers having one of the following crystallizable blocks and one of the following amorphous blocks:
Block crystallizable by nature of polyester type, such as poly(alkylene terephthalate)s, or of polyolefin type, such as polyethylenes or polypropylenes.
Amorphous and lipophilic block, such as amorphous polyolefins or copoly(olefin)s, for example poly(isobutylene), hydrogenated polybutadiene or hydrogenated poly(isoprene).

Mention may be made, as examples of such copolymers with a crystallizable block and with an amorphous block, of:
α) Poly(ε-caprolactone)-b-poly(butadiene) block copolymers, preferably used hydrogenated, such as those described in the paper D6, "Melting behavior of poly(ε-caprolactone)-block-polybutadiene copolymers", by S. Nojima, Macromolecules, 32, 3727-3734 (1999).
β) Block or multiblock hydrogenated poly(butylene terephthalate)-b-poly(isoprene) block copolymers, cited in the paper D7, "Study of morphological and mechanical properties of PP/PBT", by B. Boutevin et al., Polymer Bulletin, 34, 117-123 (1995).
γ) Poly(ethylene)-b-copoly(ethylene/propylene) block copolymers, cited in the papers D8, "Morphology of semi-crystalline block copolymers of ethylene-(ethylene-alt-propylene)", by P. Rangarajan et al., Macromolecules, 26, 4640-4645 (1993), and D9, "Polymer aggregates with crystalline cores: the system poly(ethylene)-poly(ethylene-propylene)", P. Richter et al., Macromolecules, 30, 1053-1068 (1997).

δ) Poly(ethylene)-b-poly(ethylethylene) block copolymers, cited in the general article D10, "Crystallization in block copolymers", by I. W. Hamley, Advances in Polymer Science, vol. 148, 113-137 (1999).

C) Polycondensates of Aliphatic or Aromatic or Aliphatic/Aromatic Polyester Type The polyester polycondensates can be chosen from aliphatic polyesters. Their molecular weight is preferably greater than or equal to 200 and less than or equal to 10 000 and more preferably greater than or equal to 300 and less than or equal to 5000, preferably greater than or equal to 500 and greater than or equal to 2000 g/mol.

The polyester polycondensates are chosen in particular from polycaprolactones. In particular, the polycaprolactones can be chosen from ε-caprolactone homopolymers. Homopolymerization can be initiated with a diol, in particular a diol having from 2 to 10 carbon atoms, such as diethylene glycol, 1,4-butanediol or neopentyl glycol.

Use may be made, for example, of polycaprolactones, in particular those sold under the names Capa® 240 (melting point of 68° C. and molecular weight of 4000), 223 (melting point of 48° C. and molecular weight of 2000), 222 (melting point of 48° C. and molecular weight of 2000), 217 (melting point of 44° C. and molecular weight of 1250), 2125 (melting point of 45° C. and molecular weight of 1250), 212 (melting point of 45° C. and molecular weight of 1000), 210 (melting point of 38° C. and molecular weight of 1000) and 205 (melting point of 39° C. and molecular weight of 830) by Solvay and PCL-300 and PCL-700 by Union Carbide.

Use may in particular be made of Capa® 2125, the melting point of which is between 35 and 45° C. and the weight-average molecular weight of which is equal to 1250.

The semi-crystalline polymers of the composition of the invention may or may not be partially crosslinked provided that the degree of crosslinking is not harmful to their dissolution or dispersion in the fatty phase by heating above their melting point. The crosslinking can then be chemical crosslinking, by reaction with a multifunctional monomer during the polymerization. It can also be physical crosslinking, which can then be due either to the establishment of bonds of hydrogen or dipolar type between groups carried by the polymer, such as, for example, dipolar interactions between carboxylate ionomers, these interactions being low in degree and carried by the backbone of the polymer, or to phase separation between the crystallizable blocks and the amorphous blocks carried by the polymer.

The semi-crystalline polymers of the composition according to the invention are preferably not crosslinked.

D) Copolymers of Ethylene and of Propylene Prepared by Metallocene Catalysis

The semi-crystalline polymer of the composition of the invention can also be a polymer obtained by metallocene catalysis, such as those described in patent US 2007/0 031 361, the content of which is incorporated by way of reference.

These polymers are copolymers of ethylene and of propylene prepared by metallocene catalysis, that is to say by polymerization at low pressure and in the presence of a metallocene catalyst.

The weight-average weight (Mw) of these copolymers obtained by metallocene catalysis described in this document is less than or equal to 25 000 g/mol; it ranges, for example, from 2000 to 22 000 g/mol and better still from 4000 to 20 000 g/mol.

The number-average weight (Mn) of these copolymers obtained by metallocene catalysis described in this document is preferably less than or equal to 15 000 g/mol; it ranges, for example, from 1000 to 12 000 g/mol and better still from 2000 to 10 000 g/mol.

The polydispersity index I of the polymer is equal to the ratio of the weight-average weight Mw to the number-average weight Mn.

Preferably, the polydispersity index of the copolymers is between 1.5 and 10, preferably between 1.5 and 5, preferably between 1.5 and 3 and better still between 2 and 2.5.

The copolymers can be obtained in a known way from the ethylene and/or propylene monomers, for example by metallocene catalysis, according to the process described in the document EP 571 882, the content of which is incorporated by way of reference.

The copolymers of ethylene and of propylene prepared by metallocene catalysis may or may not be "polar" modified (that is to say, modified so that they exhibit polar groups). The polar modified copolymers can be prepared in a known way from unmodified homopolymers and copolymers, such as those described above, by oxidation with gases comprising oxygen, such as air, or by grafting with polar monomers, such as maleic acid or acrylic acid or derivatives of these acids. These two routes, which make it possible to polar modify polyolefins obtained by metallocene catalysis, are described respectively in the documents EP 890 583 and U.S. Pat. No. 5,998,547, for example, the content of these two documents being incorporated by way of reference.

According to the present invention, the copolymers of ethylene and/or of propylene prepared by metallocene catalysis which are polar modified and which are particularly preferred are the polymers modified so that they exhibit hydrophilic properties. Mention may be made, by way of example, of homopolymers or copolymers of ethylene and/or of propylene modified by the presence of hydrophilic groups, such as maleic anhydride, acrylate, methacrylate, polyvinylpyrrolidone (PVP), and the like.

The homopolymers or copolymers of ethylene and/or of propylene modified by the presence of hydrophilic groups, such as maleic anhydride or acrylate, are particularly preferred.

Mention may be made, by way of example, of:
polypropylene polymers modified by maleic anhydride (PPMA), sold by Clariant, or polypropylene/ethylene/maleic anhydride copolymers, such as those sold by Clariant under the LicoCare name, for example LicoCare PP207 LP3349, LicoCare CM401 LP3345, LicoCare CA301 LP3346 and LicoCare CA302 LP3347.

In the context of a composition for the lips, preference will be given to a polar modified polymer exhibiting a low degree of crystallinity, preferably of less than 40%.

Wax

The composition in accordance with the present invention advantageously comprises less than 10% by weight of wax, indeed even less than 7% by weight or even less than 5% by weight, with respect to the total weight of the composition.

According to a specific embodiment, the composition according to the invention comprises a content of wax ranging from 0.5 to 10% by weight and better still from 3 to 7% by weight, with respect to the total weight of the composition.

The wax considered in the context of the present invention is generally a lipophilic compound which is solid at ambient temperature (25° C.), which exhibits a reversible solid/liquid change in state and which has a melting point of greater than or equal to 30° C. which can range up to 200° C. and in particular up to 120° C.

In particular, the waxes suitable for the invention can exhibit a melting point of greater than or equal to 45° C. and in particular of greater than or equal to 55° C.

Within the meaning of the invention, the melting point corresponds to the temperature of the most endothermic peak observed by thermal analysis (DSC) as described in ISO standard 11357-3; 1999. The melting point of the wax can be measured using a differential scanning calorimeter (DSC), for example the calorimeter sold under the name "MDSC 2920" by TA Instruments.

The measurement protocol is as follows:

A 5 mg sample of wax placed in a crucible is subjected to a first rise in temperature ranging from −20° C. to 100° C. at a heating rate of 10° C./minute, is then cooled from 100° C. to −20° C. at a cooling rate of 10° C./minute and, finally, is subjected to a second rise in temperature ranging from −20° C. to 100° C. at a heating rate of 5° C./minute. During the second rise in temperature, the variation in the difference in power absorbed by the empty crucible and by the crucible comprising the sample of wax is measured as a function of the temperature. The melting point of the compound is the value of the temperature corresponding to the tip of the peak of the curve representing the variation in the difference in power absorbed as a function of the temperature.

The waxes capable of being used in the compositions according to the invention are chosen from waxes of animal, vegetable, mineral or synthetic origin, and their mixtures, which are solid at ambient temperature.

Mention may in particular be made, by way of illustration of the waxes suitable for the invention, of hydrocarbon waxes, such as beeswax, lanolin wax and Chinese insect waxes, rice bran wax, carnauba wax, candelilla wax, ouricury wax, alfa wax, berry wax, shellac wax, Japan wax and sumac wax; montan wax, orange and lemon waxes, microcrystalline waxes (such as that sold under the reference Microwax HW by Paramelt), paraffin waxes and ozokerite; polyethylene waxes, such as those sold under the names Performalene 500-L and Performalene 400 by New Phase Technologies, or the waxes obtained by the Fischer-Tropsch synthesis.

Mention may also be made of waxes obtained by catalytic hydrogenation of animal or vegetable oils having linear or branched $C_8$-$C_{32}$ fatty chains. Mention may in particular be made, among these, of isomerized jojoba oil, such as the transisomerized partially hydrogenated jojoba oil manufactured or sold by Desert Whale under the commercial reference Iso-Jojoba-50®, hydrogenated sunflower oil, hydrogenated castor oil, hydrogenated coconut oil, hydrogenated lanolin oil and di(1,1,1-trimethylolpropane) tetrastearate, sold under the name of Hest 2T-4S® by Heterene.

Mention may also be made of silicone waxes ($C_{30-45}$ alkyl dimethicone) or fluorinated waxes.

Use may also be made of the waxes obtained by hydrogenation of castor oil esterified with cetyl alcohol which are sold under the names of Phytowax Castor 16L64® and 22L73® by Sophim. Such waxes are described in application FR-A-2 792 190.

Use may be made, as wax, of a $C_{20}$-$C_{40}$ alkyl (hydroxystearyloxy)stearate (the alkyl group comprising from 20 to 40 carbon atoms), alone or as a mixture.

Such a wax is sold in particular under the names "Kester Wax K 82 P®", "Hydroxypolyester K 82 P®", "Kester Wax K 80 P®" and "Kester Wax K 82 H®" by Koster Keunen.

Mention may in particular be made, as microwaxes which can be used in the compositions according to the invention, of carnauba microwaxes, such as that sold under the name of MicroCare 350® by Micro Powders, synthetic wax microwaxes, such as that sold under the name of MicroEase 114S® by Micro Powders, the microwaxes composed of a mixture of carnauba wax and of polyethylene wax, such as those sold under the names of MicroCare 300® and 310® by Micro Powders, the microwaxes composed of a mixture of carnauba wax and of synthetic wax, such as that sold under the name MicroCare 325® by Micro Powders, polyethylene microwaxes, such as those sold under the names of Micropoly 200®, 220®, 220L® and 250S® by Micro Powders, and polytetrafluoroethylene microwaxes, such as those sold under the names of Microslip 519® and 519 L® by Micro Powders.

Oil

A composition according to the invention can comprise at least one oil.

The term "oil" is understood to mean a fatty substance which is liquid at ambient temperature (25° C.) and atmospheric pressure (760 mmHg, i.e. $10^5$ Pa).

According to an embodiment, a composition according to the invention can comprise a content of oil(s) ranging from 5 to 80% by weight, with respect to the total weight of the composition, for example from 5 to 60% by weight and preferably from 5 to 50% by weight.

According to another embodiment, a composition according to the present invention can comprise less than 20% by weight of fluid oil as defined below, in particular less than 10% by weight or less than 5% by weight, with respect to the total weight of the composition, indeed is even devoid of fluid oil.

According to yet another specific embodiment of the invention, the composition is devoid of any oil and in particular of fluid oil as defined below and of glossy oil as defined below.

Fluid Oil

Within the meaning of the invention, the expression "fluid oil" denotes an oil with a molecular weight of less than 400 g/mol and in particular varying from 100 to 390 g/mol.

This oil may or may not be volatile.

This oil can be a hydrocarbon oil or a silicone oil.

The term "volatile oil" is understood to mean, within the meaning of the invention, an oil capable of evaporating on contact with the skin or with the keratinous fiber in less than one hour, at ambient temperature and atmospheric pressure. The volatile oils of the invention are volatile cosmetic oils which are liquid at ambient temperature and which have a nonzero vapor pressure, at ambient temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "nonvolatile oil" is understood to mean an oil which remains on the skin or the keratinous fiber, at ambient temperature and atmospheric pressure, for at least several hours and which has in particular a vapor pressure of less than $10^{-3}$ mmHg (0.13 Pa).

A composition according to the invention can comprise less than 2%, indeed even less than 1%, of volatile oil or else is completely devoid of volatile oil.

Mention may be made, as example of fluid oil which can be used in the invention, of:

volatile hydrocarbon oils chosen from hydrocarbon oils having from 8 to 16 carbon atoms and in particular branched $C_8$-$C_{16}$ alkanes, such as $C_8$-$C_{16}$ isoalkanes of petroleum origin (also known as isoparaffins), such as isododecane (also known as 2,2,4,4,6-pentamethyl-heptane), isodecane, isohexadecane and, for example, the oils sold under the Isopars or Permethyl trade names, branched $C_8$-$C_{16}$ esters, isohexyl neopentanoate, and their mixtures. Other volatile hydrocarbon oils, such as petroleum distillates, in particular those sold under the name Shell Solt by Shell, can also be used;

volatile silicones, such as, for example, volatile linear or cyclic silicone oils, in particular those having a viscosity ≤8 centistokes ($8×10^{-6}$ m²/s) and having in particular from 2 to 6 silicon atoms, these silicones optionally comprising alkyl or alkoxy groups having from 1 to 10 carbon atoms. Mention may in particular be made, as volatile silicone oil which can be used in the invention, of octamethylcyclotetrasiloxane, heptamethyloctyltrisiloxane, hexamethyldisiloxane, octamethyltrisiloxane or decamethyltetrasiloxane;

synthetic esters, in particular of fatty acids, such as oils of formula $R_1COOR_2$ in which $R_1$ represents the residue of a linear or branched higher fatty acid comprising 1 to 30 carbon atoms and $R_2$ represents a hydrocarbon chain, in particular a branched hydrocarbon chain, comprising from 1 to 30 carbon atoms with $R_1+R_2<30$, such as, for example, purcellin oil (cetearyl octanoate), isononyl isononanoate, isopropyl myristate, isopropyl palmitate, $C_{12}$ to $C_{15}$ alkyl benzoate, hexyl laurate, diisopropyl adipate, 2-ethylhexyl palmitate, isostearyl isostearate; octanoates, decanoates or ricinoleates of alcohols or polyalcohols, such as propylene glycol dioctanoate; hydroxylated esters, such as isostearyl lactate or octyl hydroxystearate; or polyol esters, such as propylene glycol dioctanoate, neopentyl glycol diheptanoate or diethylene glycol diisononanoate;

fatty alcohols which are liquid at ambient temperature and which have a branched and/or unsaturated carbon chain having from 8 to 26 carbon atoms, such as oleyl alcohol, linoleyl or linolenyl alcohol, isostearyl alcohol or octyldodecanol, such as sold under the commercial reference Eutanol G® by Cognis;

higher fatty acids, such as oleic acid, linoleic acid or linolenic acid;

carbonates;

acetates;

citrates;

silicone oils, such as polydimethylsiloxanes (PDMSs); and their mixtures.

Glossy Oil

A composition according to the invention can comprise at least one glossy oil.

More specifically, the term "glossy oil" according to the invention is understood to mean a hydrocarbon or silicone oil with a molecular weight of greater than 400 g/mol, indeed even of greater than 500 g/mol, in particular of greater than 650 g/mol. In particular, this glossy oil can exhibit a molar mass ranging from 400 to 10 000 g/mol, in particular from 650 to 10 000 g/mol and more particularly varying from 650 to 5000 g/mol.

In particular, a composition comprises a sufficient amount of glossy oil(s) to provide at least a makeup performance of glossy type.

A composition according to the invention can comprise a content of glossy oil(s) ranging from 0 to 20% by weight, for example from 0 to 10% by weight, preferably from 0 to 5% by weight, with respect to the total weight of the composition.

This glossy oil can be polar or nonpolar.

This glossy oil is advantageously an oil chosen from oils with a high molar mass having in particular a molar mass ranging from 500 to 10 000 g/mol, in particular from 500 to 8000 g/mol and more particularly from 550 to 7500 g/mol.

Preferably, the glossy oil has a refractive index greater than or equal to 1.45 and in particular ranging from 1.45 to 1.6.

The glossy oil is preferably a nonvolatile oil.

Advantageously, a hydrocarbon glossy oil which can be used in the present invention can be chosen from:

lipophilic polymers, such as:
polybutylenes, such as, for example, Indopol H-100 (with a molar mass or MW=965 g/mol), Indopol H-300 (MW=1340 g/mol) or Indopol H-1500 (MW=2160 g/mol), sold or manufactured by Amoco,
hydrogenated polyisobutylenes, such as, for example, Panalane H-300 E, sold or manufactured by Amoco (MW=1340 g/mol), Viseal 20000, sold or manufactured by Synteal (MW=6000 g/mol), or Rewopal PIB 1000, sold or manufactured by Witco (MW=1000 g/mol),
polydecenes and hydrogenated polydecenes, such as, for example: Puresyn 10 (MW=723 g/mol) and Puresyn 150 (MW=9200 g/mol), sold or manufactured by Mobil Chemicals,
vinylpyrrolidone copolymers, such as, for example: the vinylpyrrolidone/1-hexadecene copolymer Antaron V-216, sold or manufactured by ISP (MW=7300 g/mol), esters, such as:
esters of linear fatty acids having a total carbon number ranging from 35 to 70, such as, for example, pentaerythrityl tetrapelargonate (MW=697 g/mol),
hydroxylated esters, such as, for example, polyglycerol-2 triisostearate (MW=965 g/mol), triisocetyl citrate (MW=864 g/mol) or diisostearyl malate (MW=639 g/mol),
aromatic esters, such as, for example, tridecyl trimellitate (MW=757 g/mol),
$C_{24}$-$C_{28}$ branched fatty acid or fatty alcohol esters, such as, for example, those described in application EP-A-0 955 039 and in particular triisoarachidyl citrate (MW=1033.76 g/mol), pentaerythrityl tetraisononanoate (MW=697 g/mol), glyceryl triisostearate (MW=891 g/mol), glyceryl tri(2-decyltetradecanoate) (MW=1143 g/mol), pentaerythrityl tetraisostearate (MW=1202 g/mol), polyglyceryl-2 tetraisostearate (MW=1232 g/mol) or pentaerythrityl tetra(2-decyltetradecanoate) (MW=1538 g/mol),
a polyester resulting from the esterification of at least one triglyceride of hydroxylated carboxylic acid(s) by an aliphatic monocarboxylic acid and by an aliphatic dicarboxylic acid which is optionally unsaturated, such as, for example, the succinic acid and isostearic acid castor oil sold under the reference Zenigloss by Zenitech,
esters of dimer diol and of dimer diacid of general formula HO—$R^1$—(—OCO—$R^2$—COO—$R^1$—)$_h$—OH, in which:

$R^1$ represents a dimer diol residue, which dimer diol is obtained by hydrogenation of dilinoleic diacid, $R^2$ represents a hydrogenated dilinoleic diacid residue, and h represents an integer varying from 1 to 9, in particular the esters of dilinoleic diacids and of dilinoleyl dimer diols sold by Nippon Fine Chemical under the trade names Lusplan DD-DA5® and DD-DA7®, oils of vegetable origin, such as, for example, sesame oil (MW=820 g/mol), and their mixtures.

The hydrocarbon glossy oil can also be a hydroxylated fatty acid triglyceride and saturated diacid oligomer.

Such an oligomer is obtained by reaction of a hydroxylated fatty acid triglyceride (such as hydrogenated castor oil) and a saturated diacid.

According to the invention, the diacid is said to be saturated when the hydrocarbon chain constituting it does not comprise an unsaturation, namely a carbon-carbon double bond. The term "diacid" is understood to mean a hydrocarbon compound comprising two carboxyl functional groups —COOH. The diacid can be a single diacid or a mixture of several diacids.

Likewise, within the meaning of the invention, the oligomer can be a mixture of several oligomers.

Mention may be made, among the saturated diacids which can be used, of sebacic acid (or 1,10-decanedioic acid), succinic acid, adipic acid, azelaic acid, octadecamethylenedicarboxylic acid and eicosanedicarboxylic acid.

More particularly, the oligomer can be an oligoester, the monomers of which are represented by the following formulae (A) for triglyceride and (B) for diacid:

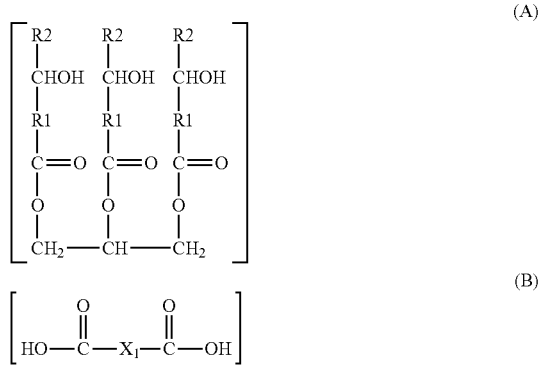

in which
R1 represents a saturated or unsaturated and linear or branched alkylene group comprising, for example, from 1 to 18 carbon atoms and R2 represents a saturated or unsaturated and linear or branched alkyl group comprising, for example, from 1 to 12 carbon atoms;
R1 preferably represents a —$(CH_2)_n$— group, where n can vary from 1 to 20 and in particular from 3 to 16, for example from 6 to 12;
R2 preferably represents a —$(CH_2)_m CH_3$ group, where m can vary from 0 to 11 and in particular from 2 to 11, for example from 3 to 9.

According to one embodiment, n=10 and m=5 and the

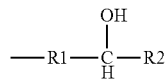

group represents the alkyl residue of 12-hydroxystearic acid (predominant component of hydrogenated castor oil);
$X_1$ is a linear or branched alkylene group, such as, for example, a linear alkylene group —$(CH_2)_x$—, where x can vary from 1 to 30 and in particular from 3 to 15.

When the diacid is sebacic acid, x is equal to 8.

The mean degree of polymerization of the oligomer can vary between 3 and 12.

The oligoester of hydrogenated castor oil and of sebacic acid is sold in particular by Croda under various names according to the degree of polymerization.

Among the oligoesters formed from hydrogenated castor oil and sebacic acid, that having a degree of polymerization of approximately 4.6 is available under the trade name "Cromadol CWS-5" and that having a degree of polymerization of approximately 9.5 is available under the trade name "Cromadol CWS-10", which are sold by Croda Japan K.K.

Mention is also made of the oligomer of hydrogenated castor oil and of sebacic acid sold under the name Crodabond-CSA (MW=3500) by Croda.

The glossy oil can also be an oil chosen from silicone oils, such as polydimethylsiloxanes (PDMSs); phenylated silicones, such as phenyl trimethicones (for example the phenyl trimethicone sold under the trade name DC556 by Dow Corning), phenyl dimethicones, phenyl(trimethylsiloxy)diphenylsiloxanes, diphenyl dimethicones, diphenyl(methyldiphenyl)trisiloxane or trimethylpentaphenyltrisiloxane (in particular 1,3,5-trimethyl-1,1,3,5,5-pentaphenyltrisiloxane, sold under the name PH-1555 HRI by Dow Corning), and their mixtures.

Preferably, the glossy oil is a hydrocarbon oil.

Fatty Phase

A composition according to the invention comprises at least one fatty phase, for example in a proportion of at least 50% by weight, in particular at least 60% by weight, especially at least 70% by weight, indeed even at least 80% by weight, with respect to the total weight of the composition.

This phase can comprise, in addition to at least one oil and/or one wax as defined above, at least one pasty compound.

Pasty Compounds

The composition according to the invention can also comprise at least one pasty compound.

The term "pasty" within the meaning of the present invention is understood to mean a lipophilic fatty compound with a reversible solid/liquid change in state which exhibits, in the solid state, an anisotropic crystalline arrangement and which comprises, at a temperature of 23° C., a liquid fraction and a solid fraction.

In other words, the starting melting point of the pasty compound can be less than 23° C. The liquid fraction of the pasty compound, measured at 23° C., can represent from 9 to 97% by weight of the compound. At 23° C., this liquid fraction preferably represents between 15 and 85% by weight, more preferably between 40 and 85% by weight.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound to change from the solid state to the liquid state. The pasty compound is "in the solid state" when the whole of its mass is in the solid form. The pasty compound is "in the liquid state" when the whole of its mass is in the liquid form.

The enthalpy of fusion of the pasty compound is equal to the area under the curve of the thermogram obtained using a differential scanning calorimeter (DSC), such as the calorimeter sold under the name MDSC 2920 by TA Instruments, with a rise in temperature of 5 or 10° C. per minute, according to ISO standard 11357-3:1999. The enthalpy of fusion of the pasty compound is the amount of energy necessary to change the compound from the solid state to the liquid state. It is expressed in J/g.

The enthalpy of fusion consumed at 23° C. is the amount of energy absorbed by the sample to change from the solid state to the state which it exhibits at 23° C., composed of a liquid fraction and of a solid fraction.

The liquid fraction of the pasty compound measured at 32° C. preferably represents from 30 to 100% by weight of the compound, preferably from 50 to 100% by weight of the compound, more preferably from 60 to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

The pasty compound is preferably chosen from synthetic compounds and compounds of vegetable origin. A pasty compound can be obtained by synthesis from starting materials of vegetable origin.

The pasty compound can advantageously be chosen from:
i) lanolin and its derivatives,
ii) polymeric or nonpolymeric silicone compounds,
iii) polymeric or nonpolymeric fluorinated compounds,
iv) vinyl polymers, in particular:
  olefin homopolymers and olefin copolymers,
  hydrogenated diene homopolymers and copolymers,
  linear or branched and homo- or copolymeric oligomers of alkyl (meth)acrylates preferably having a $C_8$-$C_{30}$ alkyl group,
  vinylpyrrolidone/eicosene copolymers (INCI name VP/eicosene copolymer), for example sold by ISP under the trade name Ganex V220F®,
  homo- and copolymeric oligomers of vinyl ethers having $C_8$-$C_{30}$ alkyl groups,
v) fat-soluble polyethers resulting from polyetherification between one or more $C_2$-$C_{100}$ diols, preferably $C_2$-$C_{50}$ diols,
vi) esters,
vii) and their mixtures.

Preference is given, among esters, in particular to:
the esters of an oligomeric glycerol, in particular the esters of diglycerol, particularly the condensates of adipic acid and of glycerol, for which a portion of the hydroxyl groups of the glycerols have reacted with a mixture of fatty acids, such as stearic acid, capric acid, isostearic acid and 12-hydroxystearic acid, such as, in particular, bis-diglyceryl polyacyladipate-2, in particular as sold under the Softisan 649® brand by Sasol,
the arachidyl propionate sold under the Waxenol 801 brand by Alzo,
phytosterol esters,
triglycerides of fatty acids and their derivatives,
pentaerythritol esters,
noncrosslinked polyesters resulting from the polycondensation between a linear or branched $C_4$-$C_{50}$ dicarboxylic acid or polycarboxylic acid and a $C_2$-$C_{50}$ diol or polyol,
ester aliphatic esters resulting from the esterification of an aliphatic hydroxycarboxylic acid ester by an aliphatic carboxylic acid,
esters resulting from the esterification of an aliphatic acid and of a hydroxylated aliphatic ester. These esters can result from the esterification a) of an aliphatic monocarboxylic or polycarboxylic acid and b) of a hydroxylated aliphatic ester, in particular a hydroxycarboxylic acid ester,
esters of dimer diol and dimer diacid, if appropriate esterified on their free alcohol or acid functional group(s) by acid or alcohol radicals, such as bis-behenyl/isostearyl/phytosteryl dimer dilinoleyl dimer dilinoleate, sold in particular under the trade name Plandool-G® by Nippon Fine Chemical,
and their mixtures.

The choice will preferably be made, among the pasty compounds, of bis-behenyl/isostearyl/phytosteryl dimer dilinoleyl dimer dilinoleate, bis-diglyceryl polyacyladipate-2, hydrogenated castor oil dimer dilinoleate, for example Risocast-DA-L, sold by Kokyu Alcohol Kogyo, hydrogenated castor oil isostearate, for example Salacos HCIS (V-L), sold by Nisshin Oil, or their mixture.

The content of pasty compound can range from 5 to 90% by weight, in particular from 5 to 50% by weight, indeed even, in certain embodiments, from 5 to 35% by weight, with respect to the total weight of the composition.

Apart from the abovementioned compounds, a composition according to the invention can also comprise other compounds, in particular as defined below. It is understood that the amount of these ancillary compounds can be adjusted by a person skilled in the art so as not to harm the effect desired in the context of the present invention.

Other Structuring Agents

The composition according to the invention can additionally comprise structuring agents other than the wax as defined above. The term "structuring agent" is understood to mean a compound capable of increasing the viscosity of the composition incorporating it. The structuring agent makes it possible in particular to obtain a composition which can exhibit a texture ranging from fluid textures to solid textures.

Mention may in particular be made, as such, of:
organophilic clays, such as hectorites modified by a $C_{10}$ to $C_{22}$ ammonium chloride, such as hectorite modified by distearyldimethylammonium chloride, such as, for example, that sold under the name of Bentone 38V® by Elementis,
pyrogenic silicas, such as pyrogenic silicas optionally hydrophobically treated at the surface, the size of the particles of which is less than 1 μm. This is because it is possible to chemically modify the surface of the silica by chemical reaction which results in a decrease in the number of silanol groups present at the surface of the silica. Silanol groups can in particular be replaced by hydrophobic groups: a hydrophobic silica is then obtained. The hydrophobic groups can be:
1. trimethylsiloxyl groups, which are obtained in particular by treatment of pyrogenic silica in the presence of hexamethyldisilazane. Silicas thus treated are named "Silica sylilate" according to the CTFA (8th edition, 2000). They are, for example, sold under the references Aerosil R812® by Degussa or Cab-O-Sil TS-530® by Cabot,
2. dimethylsilyloxyl or polydimethylsiloxane groups, which are obtained in particular by treatment of pyrogenic silica in the presence of polydimethylsiloxane or dimethyldichlorosilane. Silicas thus treated are named "Silica dimethyl silylate" according to the CTFA (8th edition, 2000). They are, for example, sold under the references Aerosil R972® and Aerosil R974® by Degussa and Cab-O-Sil TS-610® and Cab-O-Sil TS-720® by Cabot.
alkylated guar gums (with a $C_1$-$C_6$ alkyl group), such as those described in EP-A-708114, or, for example, cellulose derivatives, such as ethylcellulose, for example that soluble under the name Ethocel® by Dow Chemical,
hydrocarbon block copolymers, preferably a block copolymer which is soluble or dispersible in a liquid fatty phase.

The hydrocarbon block copolymer can in particular be a diblock, triblock, multiblock, radial or star copolymer or their blends.

Such hydrocarbon block copolymers are described in application US-A-2002/005562 and in U.S. Pat. No. 5,221, 534.

Mention may be made, as diblock copolymer, preferably hydrogenated diblock copolymer, of styrene/ethylene-propylene copolymers, styrene/ethylene-butadiene copolymers or styrene/ethylene-butylene copolymers. Diblock copolymers are sold in particular under the name Kraton® G1701E by Kraton Polymers.

Mention may be made, as triblock copolymer, preferably hydrogenated triblock copolymer, of styrene/ethylene-propylene/styrene copolymers, styrene/ethylene-butadiene/styrene copolymers, styrene/ethylene-butylene/styrene copolymers, styrene/isoprene/styrene copolymers or styrene/butadiene/styrene copolymers. Triblock copolymers are sold in particular under the names Kraton® G1650, Kraton® G1652, Kraton® D1101, Kraton® D1102 and Kraton® D1160 by Kraton Polymers.

and their mixtures.

Such other structuring agents can be included in the composition in accordance with the invention in a content of between 0.5 and 20% by weight, in particular between 0.5 and 10% by weight, with respect to the total weight of the composition.

The compositions can also comprise at least one polymer comprising at least two groups capable of interacting via hydrogen bonding.

Polymer Comprising at Least Two Groups Capable of Interacting Via Hydrogen Bonding According to a specific embodiment, the polymer comprising at least two groups capable of interacting via hydrogen bonding is present in the composition in a total content ranging from 0.5% to 50% by weight, with respect to the total weight of the composition, preferably ranging from 5 to 50% by weight and better still ranging from 8 to 45% by weight, for example ranging from 10 to 40% by weight, with respect to the total weight of said composition.

According to the invention, the polymer comprising at least two groups capable of interacting via hydrogen bonding can belong to the following two families:
1) polymers comprising at least two groups capable of establishing hydrogen interactions, these two groups being situated in the chain of the polymer, and/or
2) polymers comprising at least two groups capable of establishing hydrogen interactions, these two groups being situated on grafts or branchings.

The term "polymer" is understood to mean, within the meaning of the invention, a compound having at least 2 repeat units and preferably at least 3 repeat units.

The term "repeat units" is understood to mean, within the meaning of the invention, a unit comprising from 2 to 80 carbon atoms, preferably from 2 to 60 carbon atoms, carrying hydrogen atoms and optionally oxygen atoms, which can be saturated or unsaturated and linear, branched or cyclic. In addition, these units each comprise from one to several nonpendant heteroatoms occurring in the polymer backbone. These heteroatoms are chosen from nitrogen, sulfur, phosphorus and silicon atoms and their combinations, optionally in combination with one or more oxygen atoms.

Preferably, these groups are chosen from amide, sulfonamide, carbamate, thiocarbamate, urea, urethane, thiourea, oxamido, guanidino and biguanidino groups and their combinations.

Mention may be made, as example of polymer comprising at least two groups capable of interacting via hydrogen bonding, of:
polymers with a weight-average molecular weight of less than 100 000, comprising a) a polymer backbone having hydrocarbon repeat units provided with at least one heteroatom, and optionally b) at least one pendant fatty chain and/or at least one end fatty chain which are optionally functionalized, which have from 6 to 120 carbon atoms and which are bonded to these hydrocarbon units, such as described in applications WO-A-02/056847 and WO-A-02/47619, the content of which is incorporated by way of reference; in particular, polyamide resins (especially comprising alkyl groups having from 12 to carbon atoms), such as those described in U.S. Pat. No. 5,783,657, the content of which is incorporated by way of reference, silicone polyamide resins, such as described in application EP-A-1 266 647 and in the French patent application filed under No. 02/16039, the content of which is incorporated by way of reference, organopolysiloxanes comprising at least one carboxyl group per unit and preferably organopolysiloxanes comprising at least two carboxyl groups per unit.

Such polymers comprising at least two groups capable of interacting via hydrogen bonding are described in particular in application EP-A-1 400 234, the content of which is incorporated by way of reference, and are described in more detail below.

Silicone Polymer

According to a first embodiment of the invention, the polymer comprising at least two groups capable of interacting via hydrogen bonding is a silicone polyamide.

The silicone polyamides are preferably solid at ambient temperature (25° C.) and atmospheric pressure (760 mmHg).

The silicone polyamides of the composition of the invention can be polymers of the polyorganosiloxane type, such as, for example, those described in the documents U.S. Pat. No. 5,874,069, U.S. Pat. No. 5,919,441, U.S. Pat. No. 6,051,216 and U.S. Pat. No. 5,981,680. According to the invention, the silicone polymers can belong to the following two families:
(1) polyorganosiloxanes comprising at least two amide groups, these two groups being situated in the chain of the polymer, and/or
(2) polyorganosiloxanes comprising at least two amide groups, these two groups being situated on grafts or branchings.

A) According to a first alternative form, the silicone polymers are polyorganosiloxanes as defined above, the amide units of which are positioned in the chain of the polymer.

The silicone polyamides can more particularly be polymers comprising at least one unit corresponding to the general formula (I):

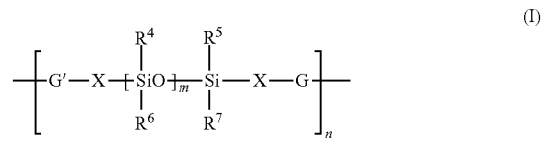

1) in which: G' represents C(O) when G represents —C(O)—NH—Y—NH—, and G' represents —NH— when G represents —NH—C(O)—Y—C(O)—, 2) $R^4$, $R^5$, $R^6$ and $R^7$, which are identical or different, represent a group chosen from:
saturated or unsaturated and linear, branched or cyclic $C_1$ to $C_{40}$ hydrocarbon groups which can comprise, in their chain, one or more oxygen, sulfur and/or nitrogen atoms and which can be partially or completely substituted by fluorine atoms,
$C_6$ to $C_{10}$ aryl groups, optionally substituted by one or more $C_1$ to $C_4$ alkyl groups, polyorganosiloxane chains, which may or may not comprise one or more oxygen, sulfur and/or nitrogen atoms, 3) the X groups, which are identical or different, represent a linear or branched $C_1$ to $C_{30}$ alkylenediyl group which can comprise, in its chain, one or more oxygen and/or nitrogen atoms, 4) Y is a saturated or unsaturated divalent $C_1$ to $C_{50}$ linear or branched alkylene, arylene, cycloalkylene, alkylarylene or arylalkylene group which can comprise one or more oxygen, sulfur and/or nitrogen atoms and/or which can carry, as substituent, one of the following atoms or groups of atoms: fluorine, hydroxyl, $C_3$ to $C_8$ cycloalkyl, $C_1$ to $C_{40}$ alkyl, $C_5$ to $C_{10}$ aryl or phenyl optionally substituted by 1 to 3 $C_1$ to $C_3$ alkyl, $C_1$ to $C_3$ hydroxyalkyl and $C_1$ to $C_6$ aminoalkyl groups, or 5) Y represents a group corresponding to the formula:

in which:

T represents a saturated or unsaturated, linear or branched and trivalent or tetravalent $C_3$ to $C_{24}$ hydrocarbon group which is optionally substituted by a polyorganosiloxane chain and which can comprise one or more atoms chosen from O, N and S, or T represents a trivalent atom chosen from N, P and Al, and $R^8$ represents a linear or branched $C_1$ to $C_{50}$ alkyl group or a polyorganosiloxane chain which can comprise one or more ester, amide, urethane, thiocarbamate, urea, thiourea and/or sulfonamide groups and which may or may not be bonded to another chain of the polymer, 6) n is an integer ranging from 2 to 500, preferably from 2 to 200, and m is an integer ranging from 1 to 1000, preferably from 1 to 700 and better still from 6 to 200.

According to one embodiment of the invention, 80% of the $R^4$, $R^5$, $R^6$ and $R^7$ groups of the polymer are preferably chosen from the methyl, ethyl, phenyl and 3,3,3-trifluoropropyl groups. According to another embodiment, 80% of the $R^4$, $R^5$, $R^6$ and $R^7$ groups of the polymer are methyl groups.

Preferably, Y represents a group chosen from:

a) linear $C_1$ to $C_{20}$, preferably $C_1$ to $C_{10}$, alkylene groups, b) branched $C_{30}$ to $C_{56}$ alkylene groups which can comprise rings and nonconjugated unsaturations, c) $C_5$-$C_6$ cycloalkylene groups, d) phenylene groups, optionally substituted by one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkyl, $C_1$ to $C_3$ hydroxyalkyl and $C_1$ to $C_6$ alkylamino groups, g) polyorganosiloxane chains of formula:

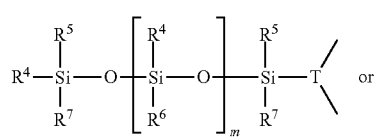 or

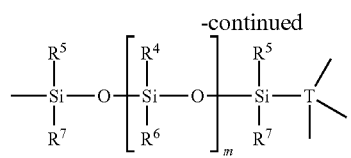

in which $R^4$, $R^5$, $R^6$ and $R^7$, T and m are as defined above.

B) According to the second alternative form, the silicone polyamides can be polymers comprising at least one unit corresponding to the formula (II):

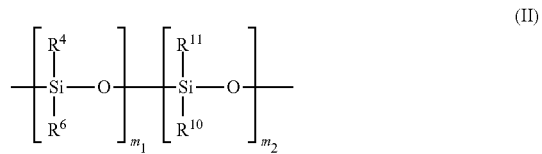

in which:

$R^4$ and $R^6$, which are identical or different, are as defined above for the formula (I), $R^{10}$ represents a group as defined above for $R^4$ and $R^6$ or represents the group of formula —X-G"-$R^{12}$, in which X are as defined above for the formula (I), $R^{12}$ represents a hydrogen atom, a saturated or unsaturated and linear, branched or cyclic $C_1$ to $C_{50}$ hydrocarbon group which optionally comprises, in its chain, one or more atoms chosen from O, S and N and which is optionally substituted by one or more fluorine atoms and/or one or more hydroxyl groups, or a phenyl group optionally substituted by one or more $C_1$ to $C_4$ alkyl groups, and G" represents —C(O)NH— and —HN—C(O)—, $R^{11}$ represents the group of formula —X-G"—$R^{12}$ in which X, G" and $R^{12}$ are as defined above, $m_1$ is an integer ranging from 1 to 998, and $m_2$ is an integer ranging from 2 to 500.

According to the invention, the silicone polymer can be a homopolymer, that is to say a polymer comprising several identical units, in particular units of formula (I) or of formula (II).

According to the invention, it is also possible to use a polymer consisting of a copolymer comprising several different units of formula (I), that is to say a polymer in which one at least of the $R^4$, $R^5$, $R^6$, $R^7$, X, G, Y, m and n values is different in one of the units. The copolymer can also be formed of several units of formula (II) in which one at least of the $R^4$, $R^6$, $R^{10}$, $R^{11}$, $m_1$ and $m_2$ values is different in one at least of the units.

It is also possible to use a polymer comprising at least one unit of formula (I) and at least one unit of formula (II), it being possible for the units of formula (I) and the units of formula (II) to be identical to or different from one another.

According to an alternative form of the invention, it is also possible to use a silicone polyamide furthermore comprising at least one hydrocarbon unit comprising two groups capable of establishing hydrogen interactions chosen from amide, sulfonamide, carbamate, thiocarbamate, urea, urethane, thiourea, oxamido, guanidino or biguanidino groups and their combinations.

These copolymers can be block polymers or grafted polymers.

In the formulae (I) and (II), the alkylene group representing X or Y can optionally comprise, in its alkylene part, at least one of the following components:

1) 1 to 5 amide, urea, urethane or carbamate groups, 2) a $C_5$ or $C_6$ cycloalkyl group, and 3) a phenylene group, optionally substituted by 1 to 3 identical or different $C_1$ to $C_3$ alkyl groups.

In the formulae (I) and (II), the alkylene groups can also be substituted by at least one component chosen from the group consisting of:
- a hydroxyl group,
- a $C_3$ to $C_8$ cycloalkyl group,
- one to three $C_1$ to $C_{40}$ alkyl groups,
- a phenyl group, optionally substituted by one to three $C_1$ to $C_3$ alkyl groups,
- a $C_1$ to $C_3$ hydroxyalkyl group, and
- a $C_1$ to $C_6$ aminoalkyl group.

In these formulae (I) and (II), Y can also represent:

where $R^8$ represents a polyorganosiloxane chain and T represents a group of formula:

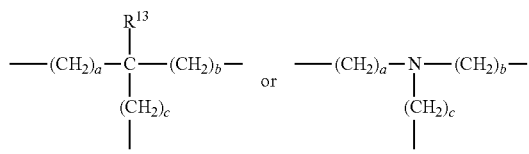

in which a, b and c are independently integers ranging from 1 to 10 and $R^{13}$ is a hydrogen atom or a group such as those defined for $R^4$, $R^5$, $R^6$ and $R^7$.

In the formulae (I) and (II), $R^4$, $R^5$, $R^6$ and $R^7$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted by one to three methyl or ethyl groups.

As was seen above, the polymer can comprise identical or different units of formula (I) or (II).

Thus, the polymer can be a polyamide comprising several units of formula (I) or (II) with different lengths, i.e. a polyamide corresponding to the formula (III):

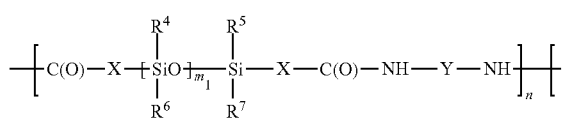

in which X, Y, n and $R^4$ to $R^7$ have the meanings given above, $m_1$ and $m_2$, which are different, are chosen within the range extending from 1 to 1000 and p is an integer ranging from 2 to 300.

In this formula, the units can be structured in order to form either a block copolymer or a random copolymer or an alternating copolymer. In this copolymer, the units may not only have different lengths but may also have different chemical structures, for example having different Y groups. In this case, the polymer can correspond to the formula (IV):

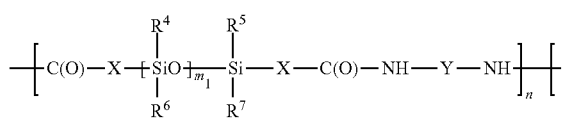

in which $R^4$ to $R^7$, X, Y, $m_1$, $m_2$, n and p have the meanings given above and $Y^1$ is different from Y but chosen from the groups defined for Y. As above, the different units can be structured in order to form either a block copolymer or a random copolymer or an alternating copolymer.

In this first embodiment of the invention, the silicone polymer can also be composed of a grafted copolymer. Thus, the polyamide comprising silicone entities can be grafted and optionally crosslinked by silicone chains comprising amide groups. Such polymers can be synthesized with trifunctional amines.

According to the invention, as was seen above, the siloxane entities can be in the main chain or backbone of the polymer but they can also be present in grafted or pendant chains. In the main chain, the siloxane entities can be in the form of segments, as described above. In the pendant or grafted chains, the siloxane entities can appear individually or in segments.

According to an alternative embodiment of the invention, it is possible to use a copolymer of silicone polyamide and of hydrocarbon polyamide, i.e. a copolymer comprising units of formula (I) or (II) and hydrocarbon polyamide units. In this case, the silicone polyamide units can be positioned at the ends of the hydrocarbon polyamide.

Advantageously, the composition comprises at least one polyamide/polydimethylsiloxane polymer, in particular a polymer of general formula (I) having an index m with a value of greater than 50, in particular of greater than 75, especially of between 50 and 200 and, for example, of approximately 100.

Advantageously, the silicone polyamide of formula (I) has a weight-average molecular weight ranging from 10 000 to 500 000 g/mol.

More preferably, X and Y independently represent a group chosen from linear $C_1$ to $C_{20}$, preferably $C_1$ to $C_{10}$, alkylene groups.

Mention may be made, as examples of polymer which can be used, of one of the silicone polyamides obtained in accordance with examples 1 to 3 of the document U.S. Pat. No. 5,981,680, such as the product sold under the reference DC 2-8179 by Dow Corning.

According to an alternative embodiment of the invention, the polymer consists of a homopolymer or copolymer comprising urethane or urea groups. These polymers are described in detail in application WO 2003/106614.

The first composition can comprise, instead of the silicone polyamide, a polyorganosiloxane polymer comprising two or

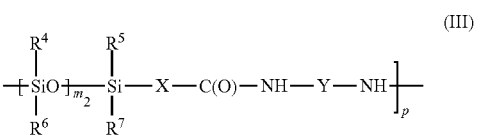

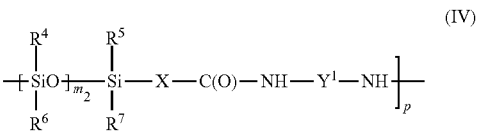

more urethane and/or urea groups, either, on the one hand, in the backbone of the polymer or, on the other hand, on side chains or as pendant groups.

The polymers comprising at least two urethane and/or urea groups in the backbone can be polymers comprising at least one unit corresponding to the following formula:

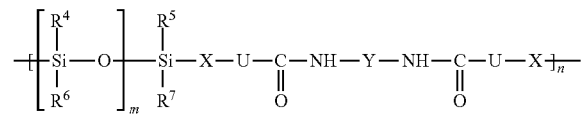

in which the $R^4$, $R^5$, $R^6$, $R^7$, X, Y, m and n groups have the meanings given above for the formula (I) and U represents —O— or —NH—, in order for:

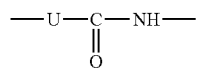

to correspond to a urethane or urea group.

In this formula, Y can be a linear or branched $C_1$ to $C_{40}$ alkylene group optionally substituted by a $C_1$ to $C_{15}$ alkyl group or a $C_5$ to $C_{10}$ aryl group. Preferably, a —$(CH_2)_6$— group is used.

The polymer constituting the silicone polymer can be formed of silicone-urethane and/or silicone-urea units which are different in length and/or in composition and can be provided in the form of block or random (statistical) copolymers.

As in the case of the silicone polyamides of formula (I), (II) or (III), use may be made, in the invention, of silicone polyurethanes or polyureas having units which are different in length and in structure, in particular units with different lengths by the number of silicone entities.

The polymers and copolymers used in the composition of the invention advantageously have a temperature for transition from the solid state to the liquid state ranging from 45° C. to 190° C. Preferably, they exhibit a temperature for transition from the solid state to the liquid state ranging from 70 to 130° C. and better still from 80° C. to 105° C.

The silicone polyamide can be present in the first composition in a total content ranging from 0.5 to 70% by weight, with respect to the total weight of the composition, preferably ranging from 5 to 50% by weight and better still ranging from 8 to 45% by weight, preferably ranging from 10 to 40% by weight, of the total weight of said composition.

Hydrocarbon Polymer

According to a second embodiment of the invention, the polymer comprising at least two groups capable of interacting via hydrogen bonding is a polymer with a weight-average molecular weight of less than 100 000 comprising a) a polymer backbone having hydrocarbon repeat units provided with at least one heteroatom and optionally b) at least one pendant fatty chain and/or at least one end fatty chain which are optionally functionalized, which have from 6 to 120 carbon atoms and which are bonded to these hydrocarbon units, such as described in applications WO-A-02/056847 and WO-A-02/47619, the content of which is incorporated by way of reference; in particular polyamide resins (especially comprising alkyl groups having from 12 to 22 carbon atoms), such as those described in U.S. Pat. No. 5,783,657, the content of which is incorporated by way of reference.

The polymer according to the invention is a nondeformable solid at ambient temperature (25° C.).

The term "functionalized chains" is understood to mean, within the meaning of the invention, an alkyl chain comprising one or more functional or reactive groups chosen in particular from hydroxyl, ether, oxyalkylene or polyoxyalkylene, halogen or ester groups, the halogen groups including fluorinated or perfluorinated groups. In addition, the hydrogen atoms of one or more fatty chains can be at least partially replaced by fluorine atoms.

Preferably, the hydrocarbon repeat units comprise at least one nitrogen atom, in particular a nonpendant nitrogen atom. In addition, these units advantageously comprise a carbonyl group.

The units comprising a heteroatom are in particular amide units, forming a backbone of the polyamide type, or carbamate and/or urea units, forming a polyurethane, polyurea and/or polyurea-urethane backbone. These units are preferably amide units. The pendant chains are advantageously bonded directly to one at least of the heteroatoms of the polymer backbone.

This polymer can comprise oxyalkylenated units between the hydrocarbon units.

In addition, this polymer of the composition of the invention advantageously comprises from 40 to 98% of fatty chains, with respect to the total number of the units comprising a heteroatom and of the fatty chains, and better still from 50 to 95%. The nature and the proportion of the units comprising a heteroatom depends on the nature of the fatty phase and is in particular similar to the polar nature of the fatty phase. Thus, the more the units comprising a heteroatom increase in polarity and in proportion in this polymer, which corresponds to the presence of several heteroatoms, the greater the affinity of this polymer for polar oils. On the other hand, the more the units comprising a heteroatom decrease in polarity, indeed even become nonpolar, or in proportion, the greater the affinity of this polymer for nonpolar oils.

This polymer is advantageously a polyamide. Another subject matter of the invention is consequently a composition comprising, in a cosmetically acceptable medium, at least one polyamide polymer with a weight-average molecular weight of less than 100 000 comprising a) a polymer backbone having amide repeat units and b) optionally at least one pendant fatty chain and/or at least one end fatty chain which are optionally functionalized, which have from 8 to 120 carbon atoms and which are bonded to these amide units.

Preferably, the pendant fatty chains are bonded to one at least of the nitrogen atoms of the amide units of this polymer.

In particular, the fatty chains of this polyamide represent from 40 to 98% of the total number of the amide units and of fatty chains and better still from 50 to 95%.

Advantageously, this polymer and in particular this polyamide of the composition according to the invention exhibits a weight-average molecular weight of less than 100 000 (in particular ranging from 1000 to 100 000), especially of less than 50 000 (in particular ranging from 1000 to 50 000) and more particularly ranging from 1000 to 30 000, preferably from 2000 to 20 000 and better still from 2000 to 10 000.

This polymer and in particular this polyamide is insoluble in water, in particular at 25° C. It especially does not comprise an ionic group.

Mention may be made, as preferred polymers which can be used in the invention, of polyamides branched by pendant fatty chains and/or end fatty chains having from 6 to 120 carbon atoms and better still from 8 to 120 carbon atoms and in particular from 12 to 68 carbon atoms, each end fatty chain being bonded to the polyamide backbone via at least one connecting group, in particular an ester group. Preferably, these polymers comprise a fatty chain at each end of the polymer backbone and in particular of the polyamide backbone. Mention may be made, as other connecting group, of ether, amine, urea, urethane, thioester, thiourea or thiourethane groups.

These polymers are preferably polymers resulting from a polycondensation between a dicarboxylic acid having at least 32 carbon atoms (having in particular from 32 to carbon atoms) with an amine chosen from diamines having at least 2 carbon atoms (in particular from 2 to 36 carbon atoms) and triamines having at least 2 carbon atoms (in particular from 2 to 36 carbon atoms). The diacid is preferably a dimer resulting from a fatty acid comprising ethylenic unsaturation having at least 16 carbon atoms, preferably from 16 to 24 carbon atoms, such as oleic acid, linoleic acid or linolenic acid. The diamine is preferably ethylenediamine, hexylenediamine or hexamethylenediamine. The triamine is, for example, ethylenetriamine. For the polymers comprising one or two end carboxylic acid groups, it is advantageous to esterify them with a monoalcohol having at least 4 carbon atoms, preferably from 10 to 36 carbon atoms and better still from 12 to 24 carbon atoms and even better still from 16 to 24 carbon atoms, for example 18 carbon atoms.

These polymers are more especially those described in the document U.S. Pat. No. 5,783,657 of Union Camp. Each of these polymers satisfies in particular the following formula (I):

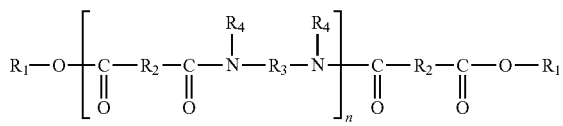

in which n denotes a whole number of amide units, such that the number of ester groups represents from 10 to 50% of the total number of the ester and amide groups; $R_1$ is independently, in each case, an alkyl or alkenyl group having at least 4 carbon atoms and in particular from 4 to 24 carbon atoms; $R_2$ independently represents, in each case, a $C_4$ to $C_{42}$ hydrocarbon group, provided that 50% of the $R_2$ groups represent a $C_{30}$ to $C_{42}$ hydrocarbon group; $R_3$ independently represents, in each case, an organic group provided with at least 2 carbon atoms, with hydrogen atoms and optionally with one or more oxygen or nitrogen atoms; and $R_4$ independently represents, in each case, a hydrogen atom, a $C_1$ to $C_{10}$ alkyl group or a direct bond to $R_3$ or to another $R_4$, so that the nitrogen atom to which both $R_3$ and $R_4$ are bonded forms part of a heterocyclic structure defined by $R_4$—N—$R_3$, with at least 50% of the $R_4$ groups representing a hydrogen atom.

In the specific case of the formula (I), the optionally functionalized end fatty chains within the meaning of the invention are end chains bonded to the final heteroatom, in this instance nitrogen, of the polyamide backbone.

In particular, the ester groups of the formula (I), which form part of the end and/or pendant fatty chains within the meaning of the invention, represent from 15 to 40% of the total number of the ester and amide groups and better still from 20 to 35%. Furthermore, n advantageously represents an integer ranging from 1 to 5 and better still greater than 2. Preferably, $R_1$ is a $C_{12}$ to $C_{22}$ alkyl group and preferably a $C_{16}$ to $C_{22}$ alkyl group. Advantageously, $R_2$ can be a $C_{10}$ to $C_{42}$ hydrocarbon (alkylene) group. Preferably, 50% at least and better still at least 75% of the $R_2$ groups are groups having from 30 to 42 carbon atoms. The other $R_2$ groups are hydrogenated $C_4$ to $C_{19}$ and even $C_4$ to $C_{12}$ groups. Preferably, $R_3$ represents a $C_2$ to $C_{36}$ hydrocarbon group or a polyoxyalkylene group and $R_4$ represents a hydrogen atom. Preferably, $R_3$ represents a $C_2$ to $C_{12}$ hydrocarbon group.

The hydrocarbon groups can be saturated or unsaturated or linear, cyclic or branched groups. Furthermore, the alkyl and alkylene groups can be saturated or unsaturated and linear or branched groups.

In general, the polymers of formula (I) are provided in the form of blends of polymers, it being possible for these blends additionally to comprise a synthetic product corresponding to a compound of formula (I) where n has the value 0, that is to say a diester.

Mention may be made, as example of polymers comprising at least two groups capable of interacting via hydrogen bonding which can be used in the compositions according to the invention, of the commercial products sold by Arizona Chemical under the names Uniclear 80 and Uniclear 100. They are sold respectively in the form of an 80% (as active material) gel in a mineral oil and a 100% (as active material) gel. They have a softening point of 88 to 94° C. These commercial products are a blend of copolymers of a $C_{36}$ diacid condensed with ethylenediamine, with a weight-average molecular weight of approximately 6000. The end ester groups result from the esterification of the remaining acid endings with cetyl alcohol, stearyl alcohol or their mixtures (also known as cetearyl alcohol).

Mention may also be made, as polymer comprising at least two groups capable of interacting via hydrogen bonding which can be used in the compositions according to the invention, of polyamide resins resulting from the condensation of an aliphatic dicarboxylic acid and of a diamine (including compounds having more than 2 carbonyl groups and 2 amine groups), the carbonyl and amine groups of adjacent individual units being condensed via an amide bond. These polyamide resins are in particular those sold under the Versamid® brand by General Mills Inc. and Henkel Corp. (Versamid 930, 744 or 1655) or by Olin Mathieson Chemical Corp. under the Onamid® brand, in particular Onamid S or C. These resins have a weight-average molecular weight ranging from 6000 to 9000. For further information on these polyamides, reference may be made to the documents U.S. Pat. No. 3,645,705 and U.S. Pat. No. 3,148,125. More especially, Versamid® 930 or 744 is used.

It is also possible to use the polyamides sold by Arizona Chemical under the Uni-Rez references (2658, 2931, 2970, 2621, 2613, 2624, 2665, 1554, 2623, 2662) and the product sold under the reference Macromelt 6212 by Henkel. For further information on these polyamides, reference may be made to the document U.S. Pat. No. 5,500,209.

It is also possible to use polyamide resins, such as those described in U.S. Pat. No. 5,783,657 and U.S. Pat. No. 5,998,570.

The polymer present in the composition according to the invention advantageously has a softening temperature of greater than 65° C. which can range up to 190° C. It preferably exhibits a softening temperature ranging from 70 to 130° C. and better still from 80 to 105° C.

Additional Polymer

The compositions according to the invention can comprise an additional polymer which may or may not be film-forming.

In the present invention, the term "film-forming polymer" is understood to mean a polymer capable of forming, by itself alone or in the presence of an additional agent which is able to form a film, a macroscopically continuous deposited layer on keratinous substances. The composition can comprise an aqueous phase and the additional polymer can be present in this aqueous phase. In this case, the additional polymer will preferably be a polymer in dispersion or an amphiphilic or associative polymer.

The term "polymer in dispersion" is understood to mean water-insoluble polymers present in the form of particles of variable size. The polymer may or may not be crosslinked. The mean particle size is typically between 25 and 500 nm, preferably between 50 and 200 nm. The following polymers in aqueous dispersion can be used: Ultrasol 2075 from Ganz Chemical, Daitosol 5000AD from Daito Kasei, Avalure UR 450 from Noveon, DynamX from National Starch, Syntran 5760 from Interpolymer, Acusol OP 301 from Röhm & Haas or Neocryl A 1090 from Avecia.

The acrylic dispersions sold under the names Neocryl XK-90®, Neocryl A-1070®, Neocryl A-1090®, Neocryl BT-62®, Neocryl A-1079® and Neocryl A-523® by Avecia-Neoresins, Dow Latex 432® by Dow Chemical, Daitosol 5000 AD® or Daitosol 5000 SJ® by Daito Kasey Kogyo; Syntran 5760® by Interpolymer, Soltex OPT by Röhm & Haas, the aqueous dispersions of acrylic or styrene/acrylic polymers sold under the trade name Joncryl® by Johnson Polymer or else the aqueous polyurethane dispersions sold under the names Neorez R-981® and Neorez R-974® by Avecia-Neoresins, the names Avalure UR-405®, Avalure UR-410®, Avalure UR-425®, Avalure UR-450®, Sancure 875®, Sancure 861®, Sancure 878® and Sancure 2060® by Goodrich, Impranil 85® by Bayer or Aquamere H-1511® by Hydromer; the sulfopolyesters sold under the trade name Eastman AQ® by Eastman Chemical Products, or vinylic dispersions, such as Mexomer PAM® from Chimex, and their mixtures, are other examples of aqueous dispersions of particles of film-forming polymers which are dispersible in water.

The term "amphiphilic or associative polymers" is understood to mean polymers comprising one or more hydrophilic parts which render them partially soluble in water and one or more hydrophobic parts via which the polymers form an association or interact. The following associative polymers can be used: Nuvis FX1100 from Elementis, Aculyn 22, Aculyn 44 and Aculyn 46 from Röhm & Haas or Viscophobe DB1000 from Amerchol. Diblock copolymers composed of a hydrophilic block (polyacrylate, polyethylene glycol) and of a hydrophobic block (polystyrene, polysiloxane) can also be used.

The composition can comprise an oily phase and the film-forming polymer can be present in this oily phase. The polymer can then be in dispersion or in solution.

Mention may be made, as examples of nonaqueous dispersions of fat-dispersible film-forming polymer in the form of nonaqueous dispersions of polymer particles in one or more silicone and/or hydrocarbon oils, which particles can be stabilized at their surface by at least one stabilizing agent, in particular a block, grafted or random polymer, of acrylic dispersions in isododecane, such as Mexomer PAP® from Chimex, or dispersions of particles of a grafted ethylenic polymer, preferably an acrylic polymer, in a liquid fatty phase, the ethylenic polymer advantageously being dispersed in the absence of additional stabilizer at the surface of the particles, such as described in particular in the document WO 04/055081.

Mention may be made, among film-forming polymers which can be used in the composition of the present invention, of synthetic polymers of radical type or of polycondensate type, polymers of natural origin, and their blends.

The term "radical film-forming polymer" is understood to mean a polymer obtained by polymerization of monomers possessing unsaturation, in particular ethylenic unsaturation, each monomer being capable of homopolymerizing (unlike polycondensates).

The film-forming polymers of radical type can in particular be vinyl polymers or copolymers, in particular acrylic polymers.

The film-forming vinyl polymers can result from the polymerization of monomers possessing ethylenic unsaturation having at least one acid group and/or of the esters of these acidic monomers and/or of the amides of these acidic monomers.

Use may be made, as monomer carrying an acid group, of unsaturated α,β-ethylenic carboxylic acids, such as acrylic acid, methacrylic acid, crotonic acid, maleic acid or itaconic acid. Use is preferably made of (meth)acrylic acid and crotonic acid and more preferentially of (meth)acrylic acid.

The esters of acidic monomers are advantageously chosen from esters of (meth)acrylic acid (also known as (meth)acrylates), in particular alkyl (meth)acrylates, especially $C_1$-$C_{30}$ alkyl (meth)acrylates, preferably $C_1$-$C_{20}$ alkyl (meth)acrylates, aryl (meth)acrylates, in particular $C_6$-$C_{10}$ aryl (meth)acrylates, or hydroxyalkyl (meth)acrylates, in particular $C_2$-$C_6$ hydroxyalkyl (meth)acrylates.

The film-forming polymer can be chosen from polymers and/or block or random copolymers comprising in particular polyurethanes, polyacrylics, silicones, fluoropolymers, butyl rubbers, ethylene copolymers, natural rubbers and polyvinyl alcohols, and their blends.

The film-forming vinyl polymers can also result from the homopolymerization or from the copolymerization of monomers chosen from vinyl esters and styrene monomers.

Mention may be made, as examples of vinyl esters, of vinyl acetate, vinyl neodecanoate, vinyl pivalate, vinyl benzoate and vinyl t-butylbenzoate.

Mention may be made, as styrene monomers, of styrene and α-methylstyrene.

Mention may be made, among film-forming polycondensates, of polyurethanes, polyesters, polyesteramides, polyamides, epoxy ester resins or polyureas.

The polyurethanes can be chosen from anionic, cationic, nonionic or amphoteric polyurethanes, polyurethane-acrylics, polyurethane-polyvinylpyrrolidones, polyester-polyurethanes, polyether-polyurethanes, polyureas, polyurea-polyurethanes, and their blends.

The polyesters can be obtained in a known way by polycondensation of dicarboxylic acids with polyols, in particular diols.

According to an example of a composition according to the invention, the film-forming polymer can be a polymer dissolved in a liquid fatty phase comprising oils or organic solvents (the film-forming polymer is then described as a fat-soluble polymer). Preferably, the liquid fatty phase comprises a volatile oil, optionally as a mixture with a nonvolatile oil.

Mention may be made, as examples of fat-soluble polymer, of copolymers of a vinyl ester (the vinyl group being directly connected to the oxygen atom of the ester group and the vinyl ester having a saturated, linear or branched, hydrocarbon radical of 1 to 19 carbon atoms bonded to the carbonyl of the ester group) and of at least one other monomer which can be a vinyl ester (other than the vinyl ester already present), an α-olefin (having from 8 to 28 carbon atoms), an alkyl vinyl ether (the alkyl group of which comprises from 2 to 18 carbon atoms) or an allyl or methallyl ester (having a saturated, linear or branched, hydrocarbon radical of 1 to 19 carbon atoms bonded to the carbonyl of the ester group).

These copolymers can be crosslinked using crosslinking agents which can be either of the vinyl type or of the allyl or methallyl type, such as tetraallyloxyethane, divinylbenzene, divinyl octanedioate, divinyl dodecanedioate and divinyl octadecanedioate.

Mention may be made, as example of fat-soluble film-forming polymers, of copolymers of a vinyl ester and of at least one other monomer which can be a vinyl ester, in particular vinyl neodecanoate, vinyl benzoate and vinyl t-butyl-benzoate, an α-olefin, an alkyl vinyl ether or an allyl or methallyl ester.

Mention may also be made, as fat-soluble film-forming polymers, of fat-soluble copolymers and in particular those resulting from the copolymerization of vinyl esters having from 9 to 22 carbon atoms or of alkyl acrylates or methacrylates, the alkyl radicals having from 10 to 20 carbon atoms.

Such fat-soluble copolymers can be chosen from copolymers of poly(vinyl stearate), of poly(vinyl stearate) crosslinked using divinylbenzene, diallyl ether or diallyl phthalate, copolymers of poly(stearyl (meth)acrylate), of poly(vinyl laurate), of poly(lauryl (meth)acrylate), it being possible for these poly(meth)acrylates to be crosslinked using ethylene glycol dimethacrylate or tetraethylene glycol dimethacrylate.

The fat-soluble copolymers defined above are known and are described in particular in application FR-A-2 232 303; they can have a weight-average molecular weight ranging from 2000 to 500 000 and preferably from 4000 to 200 000.

Mention may also be made, as fat-soluble film-forming polymers which can be used in the invention, of polyalkylenes and in particular copolymers of $C_2$-$C_{20}$ alkenes, such as polybutene, or alkylcelluloses with a saturated or unsaturated and linear or branched $C_1$ to $C_8$ alkyl radical, such as ethylcellulose and propylcellulose.

The composition according to the invention can comprise a plasticizing agent which promotes the formation of a a film with the film-forming polymer. Such a plasticizing agent can be chosen from any compound known to a person skilled in the art as being capable of fulfilling the desired purpose.

Silicone Resin

The compositions according to the invention can also comprise a silicone resin.

More generally, the term "resin" is understood to mean a compound having a three-dimensional structure. "Silicone resins" are also known as "siloxane resins". Thus, within the meaning of the present invention, a polydimethylsiloxane is not a silicone resin.

The nomenclature of silicone resins (also known as siloxane resins) is known under the name of "MDTQ", the resin being described as a function of the various monomeric siloxane units which it comprises, each of the letters "MDTQ" characterizing one type of unit.

The letter "M" represents the Monofunctional unit of formula $R1R2R3SiO_{1/2}$, the silicon atom being connected to just one oxygen atom in the polymer comprising this unit.

The letter "D" means a Difunctional unit $R1R2SiO_{2/2}$, in which the silicon atom is connected to two oxygen atoms.

The letter "T" represents a Trifunctional unit of formula $R1SiO_{3/2}$.

Such resins are described, for example, in "Encyclopedia of Polymer Science and Engineering", vol. 15, John Wiley and Sons, New York (1989), pp. 265-270, and U.S. Pat. No. 2,676,182, U.S. Pat. No. 3,627,851, U.S. Pat. No. 3,772,247, U.S. Pat. No. 5,248,739 or U.S. Pat. No. 5,082,706, U.S. Pat. No. 5,319,040, U.S. Pat. No. 5,302,685 and U.S. Pat. No. 4,935,484.

In the M, D and T units defined above, R, namely R1, R2 and R3, represents a hydrocarbon (in particular alkyl) radical having from 1 to 10 carbon atoms, a phenyl group, a phenylalkyl group or a hydroxyl group.

Finally, the letter "Q" means a tetrafunctional unit $SiO_{4/2}$ in which the silicon atom is bonded to four oxygen atoms themselves bonded to the remainder of the polymer.

Varied silicone resins with different properties can be obtained from these different units, the properties of these polymers varying as a function of the type of monomer (or unit), the nature and the number of the R radical, the length of the polymer chain, the degree of branching and the size of the pendent chains.

Use may be made, as silicone resins which can be used in the compositions according to the invention, for example, of silicone resins of MQ type, of T type or of MQT type.

MQ Resins:

Mention may be made, as an example of silicone resins of MQ type, of alkylsiloxysilicates of formula $[(R1)_3SiO_{1/2}]_x$ $(SiO_{4/2})_y$ (MQ units) in which x and y are integers ranging from 50 to 80 and such that the R1 group represents a radical as defined above and is preferably an alkyl group having from 1 to 8 carbon atoms or a hydroxyl group, preferably a methyl group.

Mention may be made, as example of solid silicone resins of MQ type of trimethylsiloxysilicate type, of those sold under the reference SR 1000 by General Electric, under the reference TMS 803 by Wacker, under the name "KF-7312J" by Shin-Etsu or under the name "DC 749" or "DC 593" by Dow Corning.

Mention may also be made, as silicone resins comprising siloxysilicate MQ units, of phenylalkylsiloxysilicate resins, such as phenylpropyldimethylsiloxysilicate (Silshine 151, sold by General Electric). The preparation of such resins is described in particular in U.S. Pat. No. 5,817,302.

T Resins:

Mention may be made, as an example of silicone resins of T type, of polysilsesquioxanes of formula $(RSiO_{3/2})_x$ (T units) in which x is greater than 100 and such that the R group is an alkyl group having from 1 to 10 carbon atoms, it being possible for said polysilsesquioxanes to additionally comprise Si—OH end groups.

Preferably, use may be made of polymethylsilsesquioxane resins in which R represents a methyl group, such as, for example, those sold:

by Wacker under the reference Resin MK, such as Belsil PMS MK: polymer comprising $CH_3SiO_{3/2}$ repeat units (T units), which can also comprise up to 1% by weight of $(CH_3)_2SiO_{2/2}$ units (D units) and which exhibits an average molecular weight of approximately 10 000 g/mol, or by Shin-Etsu under the reference KR-220L, which are composed of T units of formula $CH_3SiO_{3/2}$ and have Si—OH (silanol) end groups, under the reference KR-242A, which comprise 98% of T units and 2% of dimethyl D units and have Si—OH end groups, or under the reference KR-251, comprising 88% of T units and 12% of dimethyl D units and having Si—OH end groups.

MQT Resins:

Known resins comprising MQT units are in particular those mentioned in the document U.S. Pat. No. 5,110,890.

A preferred form of resins of MQT type is the MQT-propyl resins (also known as MQTPr). Such resins which can be used in the compositions according to the invention are in particular those described and prepared in application WO 2005/075542, the content of which is incorporated here by way of reference.

The MQ-T-propyl resin preferably comprises the units:
(i) $(R1_3SiO_{1/2})_a$
(ii) $(R2_2SiO_{2/2})_b$
(iii) $(R3SiO_{3/2})_c$ and
(iv) $(SiO_{4/2})_d$
with
R1, R2 and R3 independently representing a hydrocarbon (in particular alkyl) radical having from 1 to 10 carbon atoms, a phenyl group, a phenylalkyl group or also a hydroxyl group and preferably an alkyl radical having from 1 to 8 carbon atoms or a phenyl group,
a, b, c and d being molar fractions,
a being between 0.05 and 0.5,
b being between zero and 0.3,
c being greater than zero,
d being between 0.05 and 0.6,
a+b+c+d=1,
provided that more than 40 mol % of the R3 groups of the siloxane resin are propyl groups.

Preferably, the siloxane resin comprises the units:
(i) $(R1_3SiO_{1/2})_a$
(ii) $(R3SiO_{3/2})_c$ and
(iv) $(SiO_{4/2})_d$
with
R1 and R3 independently representing an alkyl group having from 1 to 8 carbon atoms, R1 preferably being a methyl group and R3 preferably being a propyl group,
a being between 0.05 and 0.5, preferably between 0.15 and 0.4,
c being greater than zero, preferably between 0.15 and 0.4,
d being between 0.05 and 0.6, preferably between 0.2 and 0.6 or also between 0.2 and 0.55,
a+b+c+d=1,
provided that more than 40 mol % of the R3 groups of the siloxane resin are propyl groups.

The siloxane resins which can be used according to the invention can be obtained by a process comprising the reaction of:
A) an MQ resin comprising at least 80 mol % of $(R1_3SiO_{1/2})_a$ and $(SiO_{4/2})_d$ units
R1 representing an alkyl group having from 1 to 8 carbon atoms, an aryl group, a carbinol group or an amino group,
a and d being greater than zero,
the ratio a/d being between 0.5 and 1.5;
and of
B) a T propyl resin comprising at least 80 mol % of $(R3SiO_{3/2})_c$ units,
R3 representing an alkyl group having from 1 to 8 carbon atoms, an aryl group, a carbinol group or an amino group,
c being greater than zero,
provided that at least 40 mol % of the R3 groups are propyl groups,
where the ratio by weight A/B is between 95:5 and 15:85; preferably, the ratio by weight A/B is 30:70.

Advantageously, the ratio by weight A/B is between 95:5 and 15:85. Preferably, the ratio A/B is less than or equal to 70:30. These preferred ratios have proved to make possible comfortable deposited layers.

Preferably, when it is present, the siloxane resin is present in the composition in a total content as resin dry matter ranging from 3 to 40% by weight, with respect to the total weight of the composition, preferably ranging from 4 to 30% by weight and better still ranging from 4 to 25% by weight.

Coloring Materials

The compositions according to the invention can advantageously comprise a coloring agent which can be chosen from water-soluble or fat-soluble dyes, pigments, pearlescent agents and their mixtures.

The composition according to the invention can in addition comprise one or more coloring materials chosen from water-soluble dyes and pulverulent coloring materials, such as pigments, pearlescent agents and glitter, well known to a person skilled in the art. The coloring materials can be present in the composition in a content ranging from 0.01 to 50% by weight, with respect to the weight of the composition, preferably from 0.01 to 30% by weight and in particular from 0.05 to 25% by weight, with respect to the total weight of the composition.

The term "pigments" should be understood as meaning white or colored and inorganic or organic particles which are insoluble in an aqueous solution and which are intended to color and/or opacify the resulting film.

The pigments can be present in a proportion of 0.01 to 20% by weight, in particular of 0.01 to 15% by weight and especially of 0.02 to 10% by weight, with respect to the total weight of the cosmetic composition.

Mention may be made, as inorganic pigments which can be used in the invention, of titanium, zirconium or cerium oxides, and also of zinc, iron or chromium oxides, ferric blue, manganese violet, ultramarine blue and chromium hydrate.

The pigment can also have a structure which can, for example, be of sericite/brown iron oxide/titanium dioxide/silica type. Such a pigment is sold, for example, under the reference Coverleaf NS or JS by Chemicals and Catalysts.

The coloring material can also comprise a pigment having a structure which can, for example, be of the type of silica microspheres comprising iron oxide. An example of a pigment exhibiting this structure is that sold by Miyoshi under the reference PC Ball PC-LL-100 P, this pigment being composed of silica microspheres comprising yellow iron oxide.

Mention may be made, among the organic pigments which can be used in the invention, of carbon black, pigments of D & C type, lakes based on cochineal carmine of barium, strontium, calcium or aluminum, or the diketopyrrolopyrroles (DPPs) described in the documents EP-A-542 669, EP-A-787 730, EP-A-787 731 and WO-A-96/08537.

The term "pearlescent agents" should be understood as meaning colored particles of any shape, which may or may not be iridescent, produced in particular by certain shellfish in their shells or synthesized, which exhibit a coloring effect by optical interference.

The pearlescent agents can be chosen from pearlescent pigments, such as titanium oxide-coated mica covered with iron oxide, titanium oxide-coated mica covered with bismuth oxychloride, titanium oxide-coated mica covered with chromium oxide or titanium oxide-coated mica covered with an organic dye, and pearlescent pigments based on bismuth oxychloride. They can also be mica particles, at the surface of which at least two successive layers of metal oxides and/or of organic coloring materials are superimposed.

Mention may also be made, as examples of pearlescent agents, of natural mica covered with titanium oxide, with iron oxide, with natural pigment or with bismuth oxychloride.

Mention may be made, among the pearlescent agents available on the market, of the Timica, Flamenco and Duochrome (mica-based) pearlescent agents sold by Engelhard, the Timiron pearlescent agents sold by Merck, the Prestige mica-based pearlescent agents sold by Eckart and the Sunshine synthetic mica-based pearlescent agents sold by Sun Chemical.

The pearlescent agents can more particularly have a yellow, pink, red, bronze, orangey, brown, gold and/or coppery color or glint.

Mention may in particular be made, by way of illustration of the pearlescent agents which can be employed in the context of the present invention, of pearlescent agents of gold color sold in particular by Engelhard under the name of Brilliant Gold 212G (Timica), Gold 222C (Cloisonne), Sparkle Gold (Timica), Gold 4504 (Chromalite) and Monarch Gold 233X (Cloisonne); bronze pearlescent agents sold in particular by Merck under the names Bronze Fine (17384) (Colorona) and Bronze (17353) (Colorona) and by Engelhard under the name Super Bronze (Cloisonne); orange pearlescent agents sold in particular by Engelhard under the names Orange 363C (Cloisonne) and Orange MCR 101 (Cosmica) and by Merck under the names Passion Orange (Colorona) and Matte Orange (17449) (Microna); brown-colored pearlescent agents sold in particular by Engelhard under the names Nu Antique Copper 340XB (Cloisonne) and Brown CL4509 (Chromalite); pearlescent agents with a copper glint sold in particular by Engelhard under the name Copper 340A (Timica); pearlescent agents with a red glint sold in particular by Merck under the name Sienna Fine (17386) (Colorona); pearlescent agents with a yellow glint sold in particular by Engelhard under the name Yellow (4502) (Chromalite); red-colored pearlescent agents with a gold glint sold in particular by Engelhard under the name Sunstone G012 (Gemtone); pink pearlescent agents sold in particular by Engelhard under the name Tan Opale G005 (Gemtone); black pearlescent agents with a gold glint sold in particular by Engelhard under the name Nu Antique Bronze 240 AB (Timica); blue pearlescent agents sold in particular by Merck under the name Matte Blue (17433) (Microna); white pearlescent agents with a silvery glint sold in particular by Merck under the name Xirona Silver; and golden green pinkish orangey pearlescent agents sold in particular by Merck under the name Indian Summer (Xirona); and their mixtures.

The term "dyes" should be understood as meaning compounds, generally organic compounds, which are soluble in fatty substances, such as oils, or in an aqueous/alcoholic phase.

The fat-soluble dyes can be chosen from Sudan red, DC Red 17, DC Green 6, β-carotene, Sudan brown, DC Yellow 11, DC Violet 2, DC Orange 5 and quinoline yellow. The water-soluble dyes are, for example, beetroot juice or methylene blue.

The cosmetic composition according to the invention can also comprise at least one material with a specific optical effect.

This effect is different from a simple conventional coloring effect, that is to say a unified and stabilized effect such as produced by conventional coloring materials, such as, for example, monochromatic pigments. Within the meaning of the invention, the term "stabilized" means devoid of an effect of variability in the color with the angle of observation or else in response to a change in temperature.

For example, this material can be chosen from particles with a metallic glint, goniochromatic coloring agents, diffracting pigments, thermochromic agents, optical brighteners and fibers, in particular interference fibers. Of course, these various materials can be combined so as to provide the simultaneous display of two effects.

The particles with a metallic glint which can be used in the invention are chosen in particular from:
 particles of at least one metal and/or of at least one metal derivative,
 particles comprising an organic or inorganic substrate, made of one or more materials, at least partially covered with at least one layer with a metallic glint comprising at least one metal and/or at least one metal derivative, and mixtures of said particles.

Mention may be made, among the metals which can be present in said particles, for example, of Ag, Au, Cu, Al, Ni, Sn, Mg, Cr, Mo, Ti, Zr, Pt, Va, Rb, W, Zn, Ge, Te, Se and their mixtures or alloys. Ag, Au, Cu, Al, Zn, Ni, Mo, Cr and their mixtures or alloys (for example, bronzes and brasses) are preferred metals.

The term "metal derivatives" denotes compounds derived from metals, in particular oxides, fluorides, chlorides and sulfides.

Mention may be made, by way of illustration of these particles, of aluminum particles, such as those sold under the names Starbrite 1200 EAC® by Siberline and Metalure® by Eckart.

Mention may also be made of metal powders formed of copper or alloy mixtures, such as the references 2844 sold by Radium Bronze, metal pigments, such as aluminum or bronze, for example those sold under the names Rotosafe 700 from Eckart, silica-coated aluminum particles sold under the name Visionaire Bright Silver from Eckart and particles formed of metal alloy, such as powders formed of bronze (copper and zinc alloy) coated with silica sold under the name Visionaire Bright Natural Gold from Eckart.

The particles can also comprise a glass substrate, such as those sold by Nippon Sheet Glass under the names Microglass Metashine.

The goniochromatic coloring agent can be chosen, for example, from interference multilayer structures and liquid crystal coloring agents.

Examples of symmetrical interference multilayer structures which can be used in compositions produced in accordance with the invention are, for example, the following structures: $Al/SiO_2/Al/SiO_2/Al$, pigments having this structure being sold by DuPont de Nemours; $Cr/MgF_2/Al/MgF_2/Cr$, pigments having this structure being sold under the name Chromaflair by Flex; $MoS_2/SiO_2/Al/SiO_2/MoS_2$; $Fe_2O_3/SiO_2/Al/SiO_2/Fe_2O_3$ and $Fe_2O_3/SiO_2/Fe_2O_3/SiO_2/Fe_2O_3$, pigments having these structures being sold under the name Sicopearl by BASF; $MoS_2/SiO_2/mica\text{-}oxide/SiO_2/MoS_2$; $Fe_2O_3/SiO_2/mica\text{-}oxide/SiO_2/Fe_2O_3$; $TiO_2/SiO_2/TiO_2$ and $TiO_2/Al_2O_3/TiO_2$; $SnO/TiO_2/SiO_2/TiO_2/SnO$; $Fe_2O_3/SiO_2/Fe_2O_3$; $SnO/mica/TiO_2/SiO_2/TiO_2/mica/SnO$, pigments having these structures being sold under the name Xirona by Merck (Darmstadt). By way of examples, these pigments can be pigments with a silica/titanium oxide/tin oxide structure sold under the name Xirona Magic by Merck, pigments with a silica/brown iron oxide structure sold under the name Xirona Indian Summer by Merck and pigments with a silica/titanium oxide/mica/tin oxide structure sold under the name Xirona Caribbean Blue by Merck. Mention may also be made of the Infinite Colors pigments from Shiseido. Different effects are obtained according to the thickness and the nature of the various layers. Thus, with the structure $Fe_2O_3/SiO_2/Al/SiO_2/Fe_2O_3$, the color changes from green-golden to red-gray for $SiO_2$ layers of 320 to 350 nm; from red to golden for $SiO_2$ layers of 380 to 400 nm; from purple to green for $SiO_2$ layers of 410 to 420 nm; and from copper to red for $SiO_2$ layers of 430 to 440 nm.

Mention may be made, as examples of pigments with a polymeric multilayer structure, of those sold by 3M under the name Color Glitter.

Use may be made, as liquid crystal goniochromatic particles, for example, of those sold by Chemx and of that sold under the name Helicone® HC by Wacker.

Filler

A composition according to the invention can comprise a filler, in particular in a total content ranging from 0.01 to 30% by weight, in particular from 0.01 to 20% by weight, for example ranging from 0.1 to 15% by weight or from 0.5 to 10% by weight, with respect to the total weight of the composition.

The term "filler" should be understood as meaning, within the meaning of the present invention, colorless or white and inorganic or synthetic particles of any shape which are insoluble in the medium of the composition, whatever the temperature at which the composition is manufactured. These fillers serve in particular to modify the rheology or the texture of the composition.

The fillers can be inorganic or organic and of any shape, platelet, spherical or oblong, whatever the crystallographic form (for example sheet, cubic, hexagonal, orthorhombic, and the like). Mention may be made of talc, mica, silica, kaolin, powders formed of polyamide (Nylon®) (Orgasol® from Atochem), of poly-β-alanine and of polyethylene, powders formed of tetrafluoroethylene polymers (Teflon®), lauroyllysine, starch, boron nitride, hollow polymeric microspheres, such as those of poly(vinylidene chloride)/acrylonitrile, for example Expancel® (Nobel Industrie), or of acrylic acid copolymers (Polytrap® from Dow Corning), silicone resin microbeads (Tospearls® from Toshiba, for example), polyorganosiloxane elastomer particles, precipitated calcium carbonate, magnesium carbonate, basic magnesium carbonate, hydroxyapatite, hollow silica microspheres (Silica Beads® from Maprecos), glass or ceramic microcapsules, or metal soaps derived from organic carboxylic acids having from 8 to 22 carbon atoms, preferably from 12 to 18 carbon atoms, for example zinc stearate, magnesium stearate, lithium stearate, zinc laurate or magnesium myristate.

The fillers can also be particles comprising a copolymer, said copolymer comprising trimethylol hexyllactone. In particular, a hexamethylene diisocyanate/trimethylol hexyllactone copolymer may be involved. Such particles are in particular available commercially, for example under the name of Plastic Powder D-400® or Plastic Powder D-800® from Toshiki.

Additional Normal Cosmetic Ingredients

The composition according to the invention can additionally comprise any normal cosmetic ingredient which can be chosen in particular from antioxidants, fragrances, preservatives, neutralizing agents, surfactants, sunscreens, sweeteners, vitamins, moisturizing agents, emollients, hydrophilic or lipophilic active principles, agents for combating free radicals, sequestering agents and their mixtures.

Of course, a person skilled in the art will take care to choose the optional additional ingredients and/or their amounts so that the advantageous properties of the composition according to the invention are not, or not substantially, detrimentally affected by the envisaged addition.

Application Devices

A description will now be given of examples of devices which make it possible, inter alia, to carry out a cosmetic treatment method comprising the stages consisting in:

a) reheating an application surface of a mass of solid product, using an artificial heat source situated outside the mass of product, in particular an application surface of a stick of product, in order to bring it to a temperature greater than that of a portion of the mass of product which is distant from the application surface and which remains solid during application, and b) applying the application surface thus reheated to a region to be treated, in particular the skin or the lips.

Figure 9:
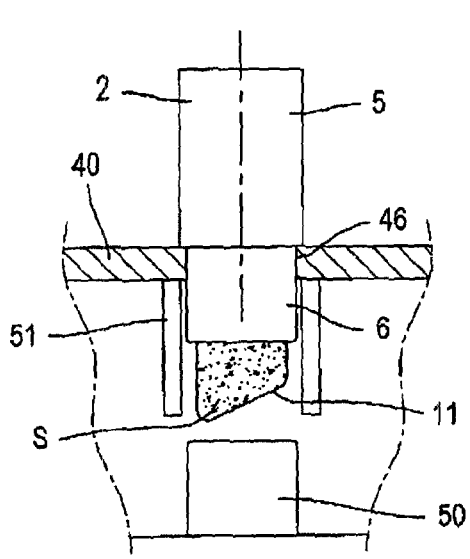
Figure 11:
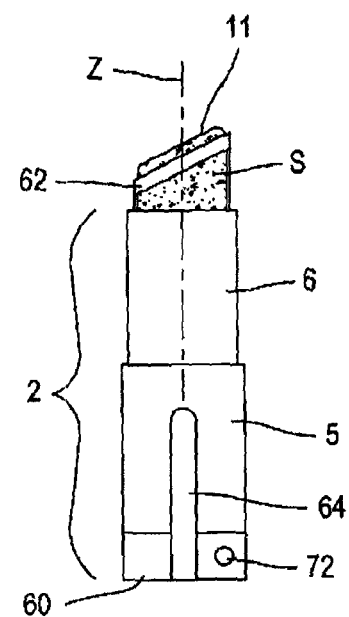

The description of these devices is made with reference to the appended drawing, in which:

FIG. 1 represents diagrammatically, in elevation, an example of a packaging and application device produced in accordance with the invention, FIG. 2 represents in isolation, with partial and diagrammatic longitudinal section, the cap of the device of FIG. 1, FIG. 3 illustrates, diagrammatically and partially, the reheating of the end of the stick by contact with a hot surface, FIG. 4 represents, diagrammatically and partially, an implementational example of the heating member, FIGS. 5 to 7 illustrate implementational details of alternative forms of heating members, FIG. 8 represents, diagrammatically, an alternative embodiment of the packaging and application device, FIG. 9 is a diagrammatic and partial section of the device of FIG. 8, after putting into the corresponding housing of the case, FIG. 10 represents a stick and associated supporting means, FIG. 11 represents, in elevation, an alternative embodiment of the packaging and application device, FIG. 12 is a partial and diagrammatic longitudinal section of the device of FIG. 11, FIG. 13 is a partial and diagrammatic longitudinal section of an alternative embodiment of the device, FIG. 14 represents an alternative form of packaging the product, and FIG. 15, described above, illustrates the measurement of the dynamic friction coefficient.

The packaging and application device 1 represented in FIG. 1 comprises a base part 2, which supports a mass of product according to the invention provided in the form of a stick S of product, and a cap 3 which can be attached to the base part 2 to close the device 1 in the absence of use.

The base part 2 can be of any known type which makes it possible to move the stick S as it is consumed.

The base part 2 comprises, for example, two parts 5 and 6 which can rotate with respect to one another and a mechanism which makes it possible to convert the relative rotation of the two parts 5 and 6 into an axial movement along the longitudinal axis X of the stick S.

The stick S is, for example, carried, within this mechanism, by a small cup 58, as represented in FIG. 10, comprising lugs 59 inserted into two components respectively belonging to parts 5 and 6, one of which comprises longitudinal rectilinear slits and the other helical slits, so that a rotation of these two components is accompanied by an axial movement of the small cup and of the stick S.

Examples of mechanisms which may be suitable are described in the publications U.S. Pat. No. 6,340,258, U.S. Pat. No. 6,086,276, U.S. Pat. No. 6,371,673, U.S. Pat. No. 5,171,096 and U.S. Pat. No. 7,293,926, the content of which is incorporated by reference.

The cap 3 comprises a heating device 10 which makes it possible to reheat the end 11 of the stick S prior to the application thereof to the keratinous substances, for example the skin or the lips.

The heating device 10 can house an invisible source of electricity, for example comprising one or more batteries or accumulators, and a heating member comprising, for example, an electric resistance fed by the source of electricity.

Examples of heating members capable of being suitable are disclosed in US 2007/0 286 665 A1, for example.

The heating member is positioned so as to raise the temperature of a heating surface 13 which, in the example of FIGS. 1 and 2, can come into contact with the stick S, as illustrated in FIG. 3, in order to raise the temperature of the distal end 11 of the stick.

The heating device 10 can comprise a switch 14 which allows the user to switch the heating device 10 on or off, and also an operating indicator 15, for example an indicator light, which comes on when the surface 13 is in the course of heating.

The heating device 10 can optionally comprise any means for regulating the temperature of the heating surface 13, in order for the temperature not to exceed a predefined value.

When the heating surface is inaccessible to the user, a higher heating temperature but one compatible with the product may be accepted. On the other hand, when the heating surface 13 may come into contact with the user, a temperature not exceeding 65° C. is preferred.

The heating device 10 can also, if appropriate, comprise a time delay which makes it possible to reheat the end 11 of the stick S only for a predefined period of time, in order to prevent premature weakening of the source of electrical energy and/or to avoid bringing the whole of the stick to an excessive temperature.

The heating device 10 can advantageously comprise any suitable sensor which makes it possible to trigger the operation of the heating only in the case of effective contact of the heating surface with the end 11 of the stick S.

For example, the heating device 10 can comprise a pressure sensor for contact between the heating surface 13 and the stick S and can allow heating of the heating surface 13 only in the case of confirmed contact with the stick S.

The heating surface 13 can be defined, for example, by a contact component 20, for example movable axially on the X axis relative to the body 22 of the heating device 10 against the return action of an elastic return member 23, such as, for example, a spring, housed inside the contact component 20, as illustrated in FIG. 4.

A heating device comprising a flattened electric resistance 25 in the bottom of the contact component 20, so as to be as close as possible to the heating surface 13, has been represented in this FIG. 4.

The contact component 20 can, for example, comprise a metal which is a good conductor of heat, with a thin wall, so as to exhibit a low thermal inertia. In some embodiments, the contact component 20 can, for example, comprise aluminum.

The heating surface 13 can be given any shape suited to the geometry of the end 11 of the stick, for example a beveled shape substantially complementary to the shape of the end 11 of the stick S, as illustrated in FIGS. 1 and 2, or another shape, for example a concave shape with regard to the stick S, in particular a sphere segment shape, as illustrated in FIG. 5, a conical or frustoconical shape, as illustrated in FIG. 6, or a shape which is substantially flat and perpendicular to the X axis, as illustrated in FIG. 7.

When the shape of the heating surface 13 is nonsymmetrical in revolution about the X axis, the device 1 can comprise means for rotationally adjusting the base part 2 and the cap 3, so as to allow the attaching of the cap 3 to the base part 2 only in a predefined angular orientation between the two, in which the heating surface 13 can be applied in a predefined way, compatible with its geometry, against the stick S.

The stick S, which is, for example, a stick of lipstick, can have a cross section of between 0.1 and 5 cm$^2$, indeed even between 0.15 and 1 cm$^2$, and the device 1 can be used by first switching on the heating device 10 and by then waiting for the period of time necessary for the end 11 of the stick which defines the application surface to be brought to the desired temperature.

That the device has been brought to the desired temperature can, for example, be indicated by the light 15, which can, for example, change from a state of being continuously lit, indicating that the device has been turned on, to a flashing light, or can change in color, when the temperature is reached. Other methods for indicating the lighting state can be employed without, however, departing from the scope of the invention.

Once the end of the stick has been reheated, the base part 2 can be separated from the cap 3 and the user can apply the product of the stick to the lips or other keratinous substances. The softening of the product at the end 11 of the stick ensures comfortable application and good transfer onto the lips with a deposited layer which is thick and optionally glossy on application.

For example, the application takes place without using an applicator. In other words, only the composition and more specifically the softened surface is brought into direct contact with the region to be treated.

The body of the stick S is at ambient temperature or at a temperature which is slightly higher but insufficient to compromise the mechanical strength necessary to withstand the mechanical stresses generated by the application. The difference in temperature between the application surface and the body of the stick, in particular at the end opposite the application surface, is, for example, at least 20° C., indeed even at least 30° C., when the stick has its starting length, at the first use.

The device 1 can be used similarly to make up the skin, it then being possible for the stick to have a greater cross section, if appropriate.

The heating device may not be incorporated in a cap 3 of the packaging device but may be present in a case 40 separate from the device for packaging the stick S as illustrated in FIGS. 8 and 9.

The case 40 can house a source of electricity and/or can comprise a means for connecting to a source of electricity, for example the mains supply, via a low-voltage transformer.

The case 40 can also comprise means for turning on 41, such as, for example, an on/off switch, and also one or more lights 42 and 55 for indicating that voltage has been applied and/or that the correct temperature has been achieved.

In the example of FIGS. 8 and 9, the case 40 comprises an opening 46 into which the base part 2 can be at least partially introduced, as illustrated in FIG. 9, in order to bring the end 11 of the stick close to a heating means 50 present in the case 40.

The opening 46 has, for example, a cross section suited to one of the components of the base part, so that the insertion of the base part into the case brings the end 11 of the stick into a predefined position, at least along two spatial directions, relative to the heating means.

The case 40 can comprise any suitable sensor 51 which makes it possible to detect that the base part 2 has been put into the case 40 and optionally to detect the positioning of the stick relative to the heating means.

The heating of the end of the stick S can take place by conduction, in contact with a hot surface, following the example of what was described above. In this case, the heating means comprises a heating surface which can be brought to the appropriate temperature by any heating means, for example an electric resistance.

The heating of the end of the stick can also be carried out without contact, for example by IR radiation and/or convection, and/or by radio frequency vibrations and/or radiation, or any other source which provides heat.

As mentioned above, the case 40 can comprise any suitable sensor, in particular optical sensor, capable of evaluating the distance between the end 11 of the stick and the heating means 50, in order to make it possible to turn the heating means 50 on only when a predefined distance is observed and/or in order to regulate the heating power according to the distance between the heating means and the end of the stick S.

In some alternative forms, the heating means 50 can be a system for heating by emission of infrared radiation towards the end 11 of the stick, for example using a halogen or incandescent lamp, or by blowing hot air towards the end 11.

In some alternative forms, the end 11 of the stick S can also be reheated by exposure to radio frequency radiation, for example microwave radiation, focused at the end 11 of the stick S.

In yet other alternative forms, the end 11 of the stick S can be reheated by ultrasonic vibrations.

In the alternative embodiment of FIGS. 11 and 12, the heating device 60 comprises a heating means 62 which is integral with the base part 2 and which can comprise, as illustrated, a heating member 62 of annular shape which can be traversed by the stick S. The heating member 62 has, for example, a cross section greater than or equal to that of the stick S.

The heating device 60 can comprise, for example, a control member 64 which the user can press in order to trigger the operation of the heating member 62. The heating member 62 can comprise, for example, a heating resistance which makes it possible to reheat, by conduction, convection and/or radiation (for example infrared radiation, microwave radiation, and the like), the end 11 of the stick S.

If appropriate, the heating member 62 can also contribute to the application of the product associated with the stick S and can, to this end, exhibit an upper face 70 of suitable shape, for example beveled.

In order to use the device in the example under consideration, the user can bring the end 11 of the stick to the level of the heating member 62 and can trigger the heating by pressing the control member 64.

The heating device can comprise an indicator light 72 which indicates to the user that the heating member 62 is operating.

The user can subsequently interrupt the heating when he observes visually that the end 11 of the stick has changed in appearance subsequent to the rise in temperature, for example has become glossy.

The user can then optionally, at this moment, move the end 11 slightly further upwards, so as to facilitate the application of the product, without contact with the heating member 62. In an alternative form, the user can apply the product to the lips or the skin with contact not only with the stick S but also with the heating member 62.

If appropriate, the surface of the heating member 62 liable to come into contact with the skin can be flocked or can exhibit a textured surface appearance which facilitates application.

In the alternative form illustrated in FIG. 13, the stick S passes through a heating member 62 defining an opening 76 with a cross section which is narrowed with respect to the cross section of the body of the stick.

The softening of the stick S in contact with the heating member 62 can thus be accompanied, in this example, by a deformation of the stick through the heating member 62. This can increase the accuracy of application of the product and can prevent the stick S from being able to be moved forwards relative to the heating member 62 when satisfactory softening has not been achieved.

The external surface of the heating member 62 can be tapered, as illustrated in FIG. 13, in order to reduce the contact surface area between the region treated and the heating member 62.

FIG. 14 represents an alternative embodiment where the mass of product S associated with the stick S is supported by a rod 200 and is suitable, for example, for single use.

The application surface 202 is reheated by being, for example, brought into contact with or close to a hot surface, for example by introducing it into a case provided with a heating means, such as the case described above with reference to FIGS. 8 and 9.

In the present text, the contents, unless expressly mentioned otherwise, are expressed by weight, with respect to the total weight of the composition.

The invention is illustrated in more detail by the examples described below, given by way of illustration and without a limiting nature. The percentages are percentages by weight. In the examples which follow, the percentages by weight are shown with respect to the total weight of the composition.

EXAMPLES

Example 1

Lipstick Compositions

| Ingredients | Function | Composition A | Composition B |
|---|---|---|---|
| Polyethylene [1] | Wax | 4.79 | 4.79 |
| Octyldodecanol [2] | Nonvolatile oil | 6.40 | — |
| Bis-diglyceryl polyacyladipate-2 [3] | Pasty compounds | 55.03 | 50.00 |
| Bis-behenyl/isostearyl/phytosteryl dimer dilinoleyl dimer dilinoleate [4] | | 22.02 | 20.00 |
| Hydrogenated castor oil isostearate [5] | | — | 15.96 |
| Poly $C_{10-30}$ alkyl acrylate [6] | Semi-crystalline polymer | 5.00 | 5.00 |
| Yellow 6 lake | Pigments | 2.06 | 1.29 |
| Blue 1 lake | | 0.13 | 0.08 |
| Red 7 | | 0.47 | 0.30 |
| Titanium dioxide [7] | | 2.19 | 1.37 |
| Iron oxides | | 0.26 | 0.16 |
| Mica (and) titanium dioxide (and) iron oxides [8] | | 1.60 | 1.00 |
| Fragrance | | 0.05 | 0.05 |
| Total | | 100 | 100 |

[1] Performalene 500-L, sold by New Phase Technologies
[2] Eutanol G, sold by Cognis
[3] Softisan 649, sold by Sasol
[4] Plandool-G, sold by Nippon Fine Chemical
[5] Salacos HCISV-L, sold by Nisshin Oillio
[6] Intelimer IPA 13-1, sold by Air Products and Chemicals
[7] Tipaque PF-671, sold by Ishihara Sangyo
[8] Cloisonne Sparkle Gold 222 J, sold by BASF The pigments of the phase C are milled in the phase A.

The millbase and the ingredients of the phase B are added to a jacketed heating vessel. The end mixture is heated at 98-100° C. while stirring with a Rayneri mixer until the ingredients have completely melted.

Finally, the pearlescent agent and the fragrance (phase D) are added to the mixture, which is cast in a mold to produce lipsticks with a diameter of 11.06 mm. The mold is subsequently placed at −20° C. for half an hour and then the sticks are removed from the mold.

The hardness at 20° C. of the stick I is 164 N·m$^{-1}$ and the hardness at 20° C. of the stick II is 187 N·m$^{-1}$.

The compositions I and II are very sticky at ambient temperature.

The beveled edge of the composition II is brought into contact with a heat source at 60° C. for 10 seconds and then applied to the lips: the application is pleasant, in comparison with the application carried out at ambient temperature as set out above. The layer deposited on the lips is thick, with a satiny gloss and with good hold of the color. The deposited layer remains comfortable over time.

The beveled edge of the composition I is brought into contact with a heat source at 60° C. for 5 seconds and then applied to the lips: the layer deposited on the lips is thick and satiny with good hold of the color. The deposited layer remains very comfortable over time.

Example 2

Lipstick Composition

| Phase | Ingredients | % by weight |
|---|---|---|
| A | Hydrogenated castor oil isostearate [1] | 15.96 |
| B | Polybutene [2] | 10.00 |
| C | Poly C$_{10-30}$ alkyl acrylate [3] | 5.00 |
|   | Polyethylene [4] | 4.79 |
|   | Bis-diglyceryl polyacyladipate-2 [5] | 42.86 |
|   | Bis-behenyl/isostearyl/phytosteryl dimer dilinoleyl dimer dilinoleate [6] | 17.14 |
| D | Yellow 6 lake | 1.29 |
|   | Blue 1 lake | 0.08 |
|   | Red 7 | 0.30 |
|   | Titanium dioxide [7] | 1.37 |
|   | Iron oxides | 0.16 |
| E | Mica (and) titanium dioxide (and) iron oxides [8] | 1.00 |
|   | Fragrance | 0.05 |
|   | Total | 100 |

[1] Salacos HCISV-L, sold by Nisshin Oillio
[2] Indopol H 100, sold by Ineos
[3] Intelimer IPA 13-1, sold by Air Products and Chemicals
[4] Performalene 500-L, sold by New Phase Technologies
[5] Softisan 649, sold by Sasol
[6] Plandool-G, sold by Nippon Fine Chemical
[7] Tipaque PF-671, sold by Ishihara Sangyo
[8] Cloisonne Sparkle Gold 222 J, sold by BASF The pigments of the phase D are milled in the phase A.

The millbase, the phase B and the ingredients of the phase C are added to a jacketed heating vessel. The combined mixture is heated at 98-100° C. while stirring with a Rayneri mixer until the ingredients have completely melted.

Finally, the pearlescent agent and the fragrance (phase E) are added to the mixture, which is cast in a mold in order to produce lipsticks with a diameter of 11.06 mm. The mold is subsequently placed at −20° C. for half an hour and then the sticks are removed from the mold.

The hardness at 20° C. of the stick is 143.5 N·m$^{-1}$.

At ambient temperature, the composition thus obtained is deposited only very slightly and is very sticky.

In order to illustrate the invention, the beveled edge of the composition is brought into contact with a heat source at 60° C. for 10 seconds and then applied to the lips: the application is pleasant, in comparison with the application carried out at ambient temperature as set out above. The layer deposited on the lips is furthermore glossy with good persistence of the glossiness.

What is claimed is:

1. A method for applying a lipstick, comprising:
   bringing an external surface of a piece of lipstick composition into contact with or into the vicinity of a heating device, the heating device comprising batteries as a source of electrical energy,
   heating said piece in a localized fashion for the purpose of softening essentially only said external surface of a piece of lipstick composition and to lower the dynamic friction coefficient thereof, and
   subsequently applying the softened external surface of the lipstick composition,
   wherein
   said lipstick composition comprises, in a physiologically acceptable medium, at least one semi-crystalline polymer.

2. The method as claimed in claim 1, wherein said semi-crystalline polymer is selected from the group consisting of:
   homopolymers and copolymers comprising units resulting from the polymerization of one or more monomers carrying crystallizable hydrophobic side chain(s),
   polymers carrying, in the backbone, at least one crystallizable block,
   polycondensates of aliphatic or aromatic or aliphatic/aromatic polyester, and
   homopolymers and/or copolymers of ethylene and/or of propylene prepared by metallocene catalysis.

3. The method as claimed in claim 1, wherein said semi-crystalline polymer is selected from the group consisting of homopolymers and copolymers resulting from the polymerization of at least one monomer with crystallizable chain(s) of formula X:

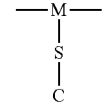

wherein
M is an atom of the polymer backbone,
S is a spacer,
C is an optionally fluorinated or perfluorinated crystallizable group having an alkyl chain with at least 12 carbon atoms,
and their blends.

4. The method as claimed in claim 1, wherein said semi-crystalline polymer is a poly((C$_{10}$-C$_{30}$)alkyl acrylate) having a weight-average molecular weight of from 15,000 to 500,000.

5. The method as claimed in claim 1, wherein said semi-crystalline polymer is present in a content of 2 to 20% by weight, with respect to the total weight of the composition.

6. The method as claimed in claim 1, wherein the lipstick composition further comprises less than 10% by weight of wax, with respect to the total weight of the composition.

7. The method as claimed in claim 1, wherein a temperature-sensitive dynamic friction coefficient of the lipstick composition is greater than or equal to 0.5 at 25° C.

8. The method as claimed in claim 1, wherein a hardness of the lipstick composition is greater than or equal to 80 N·m$^{-1}$ at 20° C.

9. The method as claimed in claim 1, wherein said dynamic friction coefficient is, at the temperature to which the lipstick composition is heated, less than or equal to 0.45.

10. The method as claimed in claim 1, wherein the lipstick composition further comprises from 5 to 90% by weight of at least one pasty compound, with respect to the total weight of the composition.

11. The method as claimed in claim 10, wherein the at least one pasty compound is selected chosen from the group consisting of (i) lanolin and its derivatives, (ii) polymeric or nonpolymeric silicone compounds, (iii) polymeric or non-polymeric fluorinated compounds, (iv) vinyl polymers, hydrogenated diene homopolymers and copolymers, linear or branched and homo- or copolymeric oligomers of alkyl (meth)acrylates, vinylpyrrolidone/eicosene copolymers, or homo- and copolymeric oligomers of vinyl ethers having $C_8$-$C_{30}$ alkyl groups, (v) fat-soluble polyethers resulting from polyetherification between one or more $C_2$-$C_{100}$ diols, (vii) and mixtures thereof.

12. The method as claimed in claim 1, wherein the lipstick composition comprises at least one coloring agent selected from the group consisting of water-soluble or fat-soluble dyes, pigments, pearlescent agents and mixtures thereof.

13. The method as claimed in claim 4, wherein the weight-average molecular weight of said poly(($C_{10}$-$C_{30}$)alkyl acrylate) is from 100,000 to 200,000.

14. The method as claimed in claim 5, wherein the content of said semi-crystalline polymer is 3 to 15% by weight, with respect to the total weight of the lipstick composition.

15. The method as claimed in claim 10, wherein the at least one pasty compound is selected from the group consisting of the esters of an oligomeric glycerol, arachidyl propionate, phytosterol esters, triglycerides of fatty acids and their derivatives, pentaerythritol esters, noncrosslinked polyesters resulting from the polycondensation between a linear or branched $C_4$-$C_{50}$ dicarboxylic acid or polycarboxylic acid and a $C_2$-$C_{50}$ diol or polyol, ester aliphatic esters resulting from the esterification of an aliphatic hydroxycarboxylic acid ester by an aliphatic carboxylic acid, esters resulting from the esterification of an aliphatic acid and of a hydroxylated aliphatic ester, esters of dimer diol and dimer diacid, optionally esterified on their free alcohol or acid functional group(s) by acid or alcohol radicals, and their mixtures.

16. The method as claimed in claim 1, wherein the lipstick composition further comprises a hydrocarbon or silicone oil with a molecular weight of greater than 400 g/mol.

17. The method as claimed in claim 10, wherein the weight % of the at least one pasty compound is from 5 to 50% by weight, with respect to the total weight of the lipstick composition.

* * * * *